(12) United States Patent
Kahn et al.

(10) Patent No.: US 6,385,546 B1
(45) Date of Patent: May 7, 2002

(54) STABILIZING AND DESTABILIZING PROTEINS

(75) Inventors: Peter C. Kahn, East Brunswick, NJ (US); Adrian Goldman; Sari Helin, both of Turku (FI)

(73) Assignee: Rutgers, The University of New Jersey, New Brunswick, NJ (US)

( * ) Notice: Subject to any disclaimer, the term of this patent is extended or adjusted under 35 U.S.C. 154(b) by 0 days.

(21) Appl. No.: 09/586,875

(22) Filed: Jun. 5, 2000

Related U.S. Application Data

(63) Continuation of application No. 08/971,004, filed on Nov. 14, 1997, now abandoned.
(60) Provisional application No. 60/030,926, filed on Nov. 15, 1996.

(51) Int. Cl.$^7$ .................................................. G01N 33/48
(52) U.S. Cl. ........................ 702/19; 435/4; 436/86; 702/22; 702/23; 702/27
(58) Field of Search ........................ 435/4, 183; 702/19, 702/23, 22, 27; 436/86

(56) References Cited

U.S. PATENT DOCUMENTS

| | | | |
|---|---|---|---|
| 4,760,025 A | 7/1988 | Estell et al. ................. | 435/222 |
| 5,422,243 A | 6/1995 | Jalkanen et al. ............... | 435/6 |
| 5,441,882 A | 8/1995 | Estell et al. ................. | 435/222 |
| 5,500,364 A | 3/1996 | Christianson et al. ........ | 435/221 |

OTHER PUBLICATIONS

Adams, M.W.W. "Enzymes and proteins from organisms that grow near and above 100° C" *Annu. Rev. Microbiol.*, 47:627–658 (1993).
Adams, et al. "Enzymes from microorganisms in extreme environments" *C&E News*, pp. 32–42 (Dec. 18, 1995).
Adams et al., M.W.W. "Extremozymes: Expanding the limits of biocatalysis" *Biotechnology* 13:662–668 (1995).
Argos et al. "Thermal stability and protein structure" *Biochemistry* 18:5698–5703 (1979).
Avigad et al. "Molecular properties of cis, cis–mucronate cycloisomerase from *Pseudomonas putida*" *J. Mol. Biol.* 89:651–662 (1974).
Baykov et al. "Dissociation of hexameric *Escherichia coli* inorganic pyrophosphatase into trimers in Ile136–>Gln or His140–>Gln substitution and its effect on enzyme catalytic properties" *J. Biol. Chem.* 270:30804–30812 (1995).
Bernstein et al. "The Protein Data Bank: A computer–based archival file for macromolecular structure" *J. Mol. Biol.* 112:535–542 (1977).
Blow et al. "The treatment of errors in the isomorphous replacement method" *Acta Crystallogr.* 12:794–802 (1959).
Borchert et al. "Design, creation, and characterization of a stable, monomeric triose phosphate isomerase" *Proc. Natl. Acad. Sci. USA* 91:1515–1518 (1994).

Brünger et al. "Crystallographic R factor refinement by molecular dynamics" *Science* 235:458–460 (1987).
Chari et al. "Absolute stereochemical course of e–carboxymuconate cycloisomerases from *Pseudomona putida* and *Acinetobacter calcoasedicus*: analysis and implications" *J. Am. Chem. Soc.* 109:5514–5519 (1987).
Chatterjee et al. Determination of Km and $K_{cat}$ for signal peptidase I using a full length secretory precursor, pro–OmpA–nuclease. *J. Mol. Biol.* 245:311–314 (1995).
Chothia, C. "Hydrophobic bonding and accessible surface area in proteins" *Nature* 248:338–339 (1974).
Chothia, C. "The nature of accessible and buried surfaces in proteins" *J. Mol. Biol.* 105:1–14 (1976).
Christensen et al. "Molten globule intermediates and protein folding" *Eur. Biophys. J.* 19:221–229 (1991).
Cuatrecasas et al. "The action of staphylococcal nuclease on synthetic substrates" *Biochemistry* 8:2277–2284 (1969).
Dill, K.A. "Dominant forces in protein folding" *Biochemistry* 29:7133–7155 (1990).
Eisenberg et al. "Solvation energy in protein folding and binding" *Nature* 319:199–203 (1986).
Eftink et al. "Dynamics of a protein matrix revealed by fluorescence quenching" *Proc. Nat. Acad. Sci. USA* 72:3290–3294 (1975).
Eriksson et al. "Response of a protein structure to cavity –creating mutations and its relationship to the hydrophobic effect" *Science* 255:178–183 (1992).
Foygel et al. "The volume changes of the molten globule transitions of horse heart ferricytochrome c: A thermodynamic cycle" *Protein Science* 4:1426–1429 (1995).
Gerlt et al. "Understanding enzyme–catalyzed proton abstraction from carbon acids: details of stepwise mechanisms for b–elimination reactions" *J. Am. Chem. Soc.* 114:5928–5934 (1992).
Gilliland et al. "The biological macromolecular crystallization database: a tool for developing crystallization strategies" *In Methods, a Companion to Methods in Enzymology* 1:6–11 (1990).

(List continued on next page.)

Primary Examiner—Nashaat T. Nashed
(74) Attorney, Agent, or Firm—Fish & Richardson P.C.

(57) ABSTRACT

The invention described herein is a method of identifying and changing amino acid residues that affect the stability of a protein and thereby to "adjust" the stability of a protein under particular conditions, e.g., to function at lower or higher temperatures. The residues modified in the method are chosen such that they are not in or interact with an active site or binding site of the protein, and therefore the mode of action or interaction of the protein on substrates remains unchanged. The method has wide applicability to any situation where a protein would be a better match to a pre-existing or new process if the functional optimum of the protein under particular conditions were different. Among others, the method is useful to produce proteins for bioremediation, food technology and enzymes for detergents.

2 Claims, 6 Drawing Sheets

OTHER PUBLICATIONS

Haynie et al. "Structural energetics of the molten globule state" *Proteins: Struct. Funct. Genet.* 16:115–140 (1993).

Heikinheimo et al. "A site directed mutagenesis study of *Saccharomyces cerevisiae* inorganic pyrophosphatase. Functional conservation of the active site of soluble inorganic pyrophosphatases" *Eur. J. Biochem.* 239(11):138–143 (1996).

Helin et al. "The refined x–ray structure of mucronate lactonizing enzyme from *Pseudomonas putida* at 1.85 A resolution" *J. Mol. Biol.* 254:918–941 (1995).

Hensel et al. "Characterization of two D–glyceraldehyde–3–phosphate dehydrogenases from the extremely thermophylic archaebacterium *Thermoproteus tenax*." *Eur. J. Biochem.* 170:325–333 (1987).

Hermann, R.B. "Theory of hydrocarbon bonding. II. The correlation of hydrocarbon solubility in water with solvent cavity surface area." *J. Phys. Chem.* 76:2754–2759 (1972).

Hendsch et al., "Do salt bridges stabilize proteins?" *Protein Sci.* 3:211–226 (1994).

Hibler et al. Site directed mutants of staphylococcal nuclease. Detection and localization by $^1$H NMR spectroscopy of conformational changes accompanying substitutions for glutamic acid 43. *Biochemistry* 26:6278–6286 (1987).

Hochachka et al. Chapter Eleven "Temperature Adaptation" "Biochemical Adaptations" Princeton University Press (1984).

Holm et al. "The FSSP Database of structurally aligned protein fold families" *Nucleic Acids Res.* 22:3600–3609 (1994).

Honig et al. "Free energy balance in protein folding" *Adv. Prot. Chem.* 46:27–58 (1995).

Hynes et al. "The crystal structure of staphylococcal nuclease refined at 1.7 A resolution." *Proteins: Struct. Funct. Genet.* 10:92–105 (1991).

Jaenicke, R. "Protein stability and molecular adaptation to extreme conditions" *Eur. J. Biochemistry* 202:715–728 (1991).

James et al. "Applications of enzymes in food processing" *Crit. Rev. Food Sci. Nutr.* 36:437–453 (1996).

Jancarik et al. "Sparse matrix sampling: a screening method for crystallization of proteins" *Appl. Cryst.* 24:409–411 (1991).

Janin, J. "Surface area of globular proteins" *J. Mol. Biol.* 105:13–14 (1976).

Jones et al. "Improved methods for building protein models in electron density maps and the location f errors in these models" *Acta Crystallogr. A* 47:110–119 (1991).

Kahn, P.C. "The interpretation of near ultraviolet circular dichroism" *Meth. Enzymol.* 61:339–378 (1979).

Käpylä et al. The effect of D97E substitution on the kinetic and thermodynamic properties of *Escherichia coli* Inorganic pyrosphosphatase *Biochemistry* 34:792–800 (1995).

Kauzmann W. "Some factors in the interpretation of protein denaturation" *Adv. Prot. Chem.* 14:1–63 (1959).

Koehl et al. "Polar and nonpolar atomic environments in the protein core: Implications for folding and binding" *Proteins: Struct. Funct. Genet.* 20:264–278 (1994).

Kuwajima, K. "The molten globule state as a clue for understanding the folding and cooperativity of globular protein structure" *Proteins: Struct. Funct. Genet.* 6:87–103 (1989).

Lee, B. "Isoenthalpic and isoentropic temperatures and the thromodynamics of protein denaturation" *Proc. Natl. Acad. Sci USA* 88:5154–5158 (1991).

Lee et al. "The interpretation of protein structures: Estimation of static accessibility" *J. Mol. Biol.* 55:379–400 (1971).

Makhatadze et al. "Energetics of protein structure" *Adv. Prot. Chem.* 47:307–425 (1995).

Makhatadze et al. "Heat capacity of proteins I. Partial molar heat capacity of individual amino acid residues in aqueous solution: Hydration effect." *J. Mol. Biol.* 213:375–384 (1990).

Matthew, J. "Electrostatic effects in proteins" *Annu. Rev. Biophys. Biophys. Chem.* 14:387–417 (1985).

Mozhaev et al. Structure stability relationship in proteins: fundamental tasks and strategy for the development of stabilized enzyme catalysts for biotechnology. *CRC Crit. Rev. Biochem.* 23:235–281 (1988).

Murphy et al. "Thermodynamics of structural stability and cooperative folding in proteins" *Adv. Prot. Chem.* 43:313–361 (1992).

Ngai et al. "Enzymes of the b–ketoadipate pathway in *Pseudomonas putida*: Kinetic and magnetic resonance studies of the cis, cis–mucronate cycloisomerase catalyzed reaction" *Biochemistry* 22:5223–5230 (1983).

Perutz et al. "Stereochemical basis of heat stability in bacterial ferredoxins and in haemoglobin A2" *Nature* 255:256–259 (1975).

Privalov, P.L. "Stability of proteins: Small globular proteins" *Adv. Prot. Chem.* 33:167–241 (1979).

Privalov, P.L. "Stability of proteins: Proteins which do not present a single cooperative system" *Adv. Prot. Chem.* 35:1–104 (1982).

Privalov et al. "Stability of protein structure and hydrophobic interaction" *Adv. Prot. Chem.* 39:191–234 (1988).

Ptitsyn, O.B. "The molten globule state" *Creighton, T.E., ed. Protein folding.* Freeman, New York pp. 243–300 (1992).

Ptitsyn, O.B. "Molten globule and protein folding" *Adv. Prot. Chem.* 47:83–229 (1995).

Rashin et al. "On the environment of ionizable groups in globular proteins" *J. Mol. Biol.* 173:515–521 (1984).

Richards, F.M. "Areas, volumes, packing and protein structures" *Annu. Rev. Biphys. Bioeng.* 6:151–176 (1977).

Sali et al. "Derivation of rules for comparative protein modeling from a database of protein structure alignments" *Prot. Sci.* 3:1582–1596 (1994).

Salminen et al. "An unusual route to thermostability disclosed by the comparison of *Thermus thermophilus* and *Eschericchia coli* inorganic pyrophosphatases" *Protein Science*, 5:1014–1025 (1996).

Shoichet et al. "A relationship between protein stability and protein function" *Proc. Natl. Acad. Sci. USA* 92:452–456 (1995).

Shortle, D. "Staphylococcal nuclease: A showcase of m–value effects" *Adv. Prot. Chem.* 46:217–247 (1995).

Shortle et al. Mutant forms of staphylococcal nuclease with altered patterns of guanidine hydrochloride and urea denaturation. *Proteins: Struct. Funct. Genet.* 1:81–89 (1986).

Spassov et al. The optimization of protein–solvent interactions: thermostability and the role of hydrophobic and electrostatic interactions *Prot. Sci.* 4:1516–1527 (1995).

Spolar et al. "Use of liquid hydrocarbon and amide transfer data to estimate contributions to thermodynamic functions of protein folding from the removal of nonpolar and polar surface from water" *Biochemistry* 31:3947–3955 (1992).

Stites et al. In a staphylococcal nuclease mutant the side chain of a lysine replacing valine 66 is fully buried in the hydrophobic core *J. Mol. Biol.* 221:7–14 (1991).

Takahara et al. "The OmpA signal peptide directed secretion of staphylococcal nuclease A by *Escherichia coli*" *J. Biol. Chem.* 260:2670–2674 (1985).

Varley et al. "Relation between stability, dynamics and enzyme activity in 3–phosphoglycerate kinases from yeast and *Thermus thermophilus*" *J. Mol. Biol.* 220:531–538 (1991).

Velichko et al. "Cold lability of mutant forms of *Escherichia coli* inorganic pyrophosphatase" *FEBS Lett.* 359:20–22 (1995).

Waldburger et al. "Are buried salt bridges important for protein stability and conformational specificity?" *Struct. Biol.* 2:122–128 (1995).

Waldburger et al. "Barriers to protein folding: Formation of buried polar interactions is a slow step in acquisition of structure" *Proc. Natl. Acad. Sci. USA* 93:2629–2634 (1996).

Warshel, Al "Energetics of enzyme catalysis" *Proc. Natl. Acad. Sci. USA* 75:5250–5254 (1978).

Warshel et al. "Evaluation of catalytic free energies in genetically modified proteins" *J. Mol. Biol.* 201:139–159 (1988).

Wrba et al. "Extremely thermostable D–glyceraldehyde–3–phosphate dehydrogenase from the eubacterium *Thermotoga maritima*" *Biochemistry* 29:7584–7592 (1990).

Wyman, J. "Linked functions and reciprocal effects in hemoglobin: A second look" *Adv. Prot. Chem.* 19:224–286 (1964).

Ybe et al. "Slow folding kinetics of ribonuclease–A by volume change and circular dichroism: Evidence for two independent reactions" *Protein Science* 3:638–649 (1994).

Zhi et al. "conformational stability of pig citrate synthase and some active site mutants" *Biochemistry* 30:9281–9286 (1991).

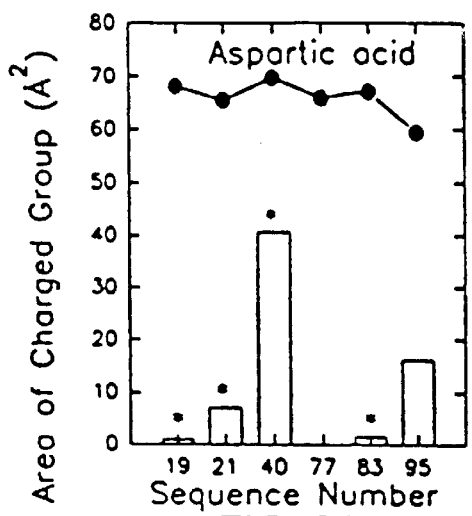
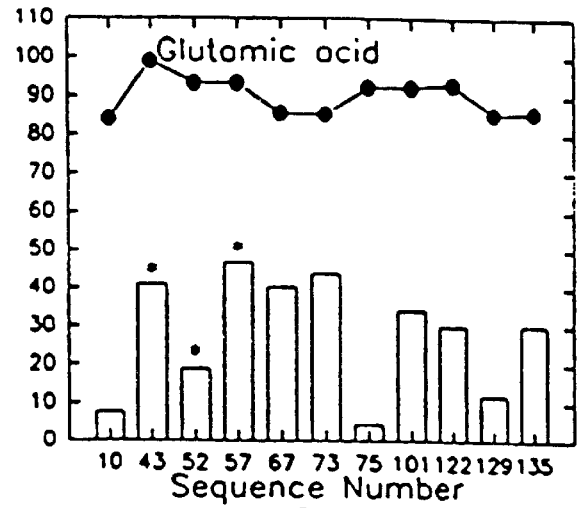
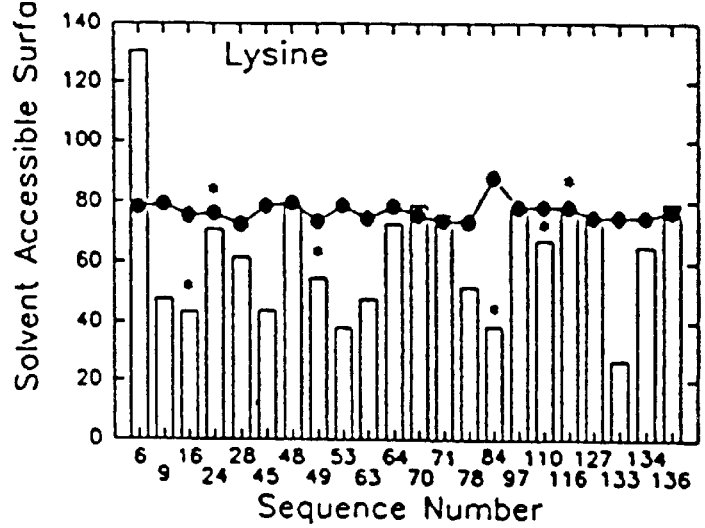
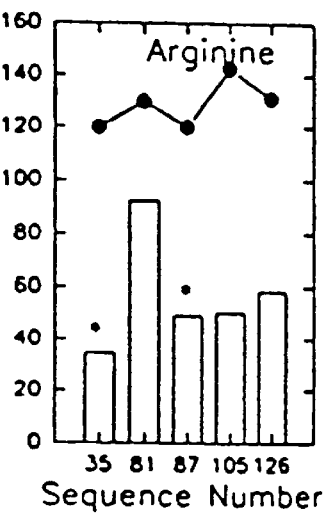
Key: Bars = Native; Filled circles = Extended
Asterisks (*) denote residues in or near the active site.
FIG. 2A
FIG. 2B
FIG. 2C
FIG. 2D

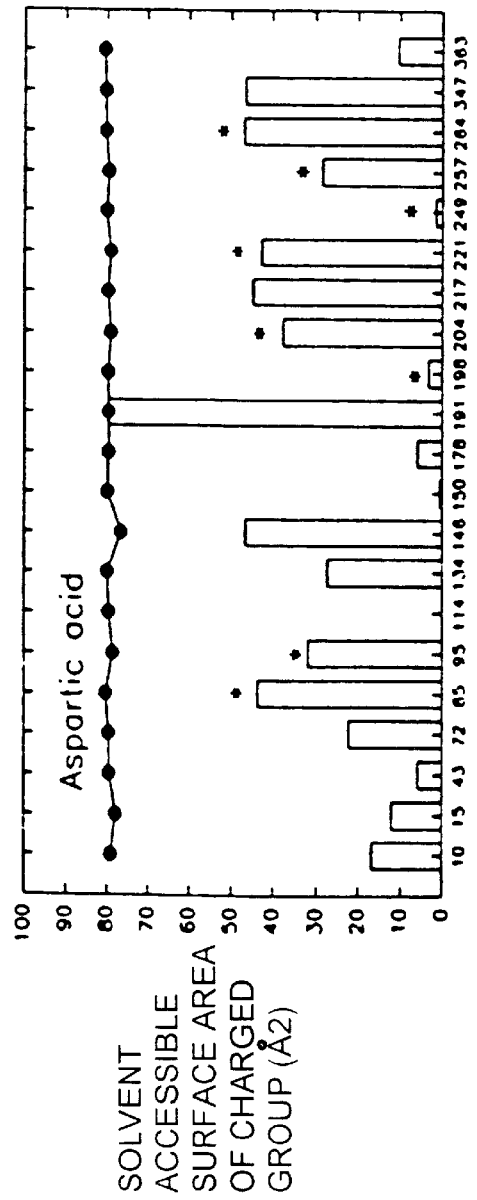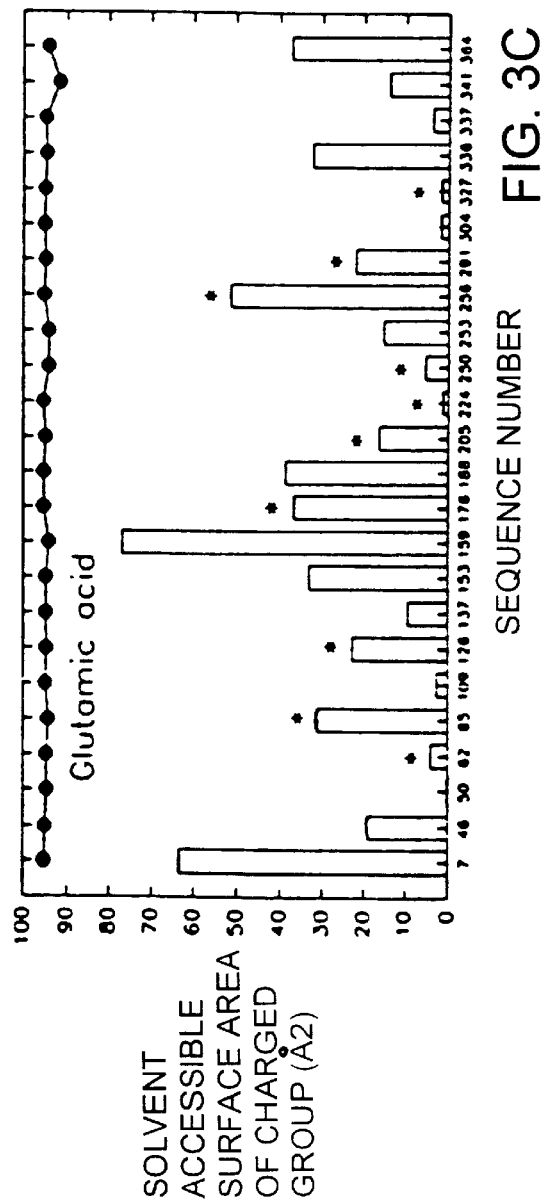

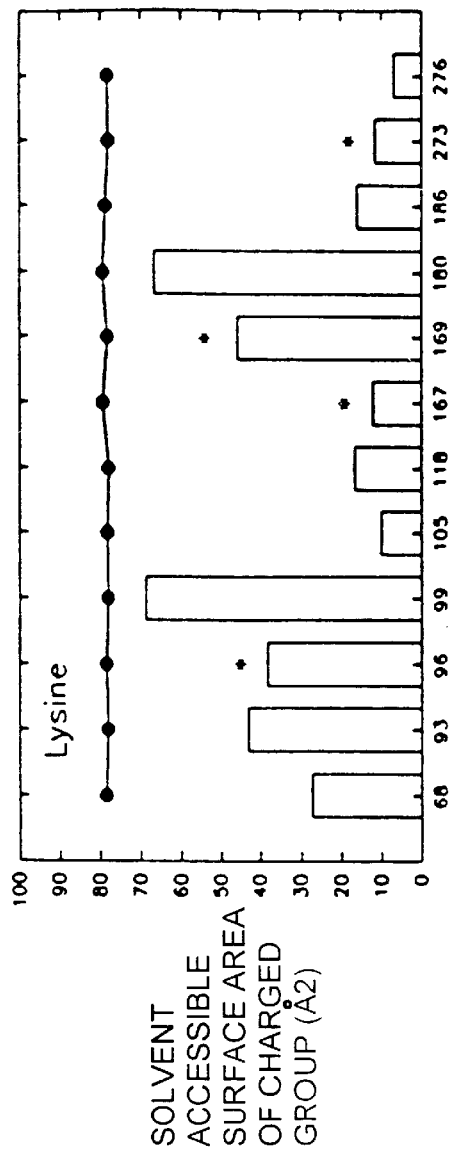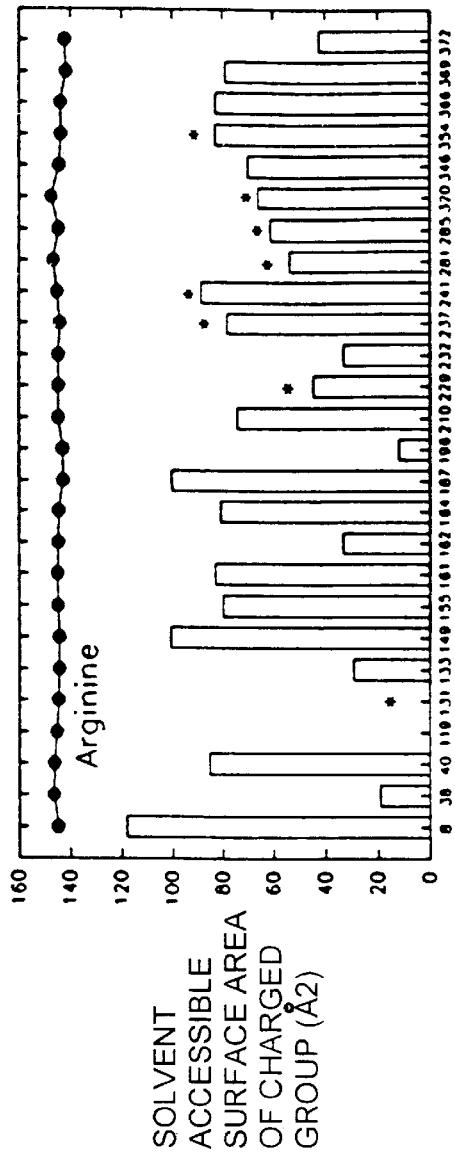

Table 1: Statistical parameters calculated for the data shown in Figure 1

| Linear Fit to %Buried = *slope* •length + *intercept* | | | | | | |
|---|---|---|---|---|---|---|
| | *Slope* | | *Intercept* | | Correlation coefficient | Probability of slope = 0 (t test)[1] |
| | Value (100 x %/aa) | Std Error | Value (%) | Std Error | | |
| Aliphatic | 3.75 | 0.32 | 56.8 | 0.9 | 0.723 | <0.0001 |
| Aromatic | 2.08 | 0.72 | 72.2 | 2.1 | 0.251 | <0.005 |
| Uncharged polar | 2.07 | 0.24 | 66.4 | 0.7 | 0.608 | <0.0001 |
| Charged polar | 4.57 | 0.49 | 36.5 | 1.4 | 0.644 | <0.0001 |

Statistical significance of pairwise differences between slopes (t test)[1].

| | Aliphatic | Aromatic | Uncharged | Charged |
|---|---|---|---|---|
| Aliphatic | * | <0.05 | <0.001 | >0.10 |
| Aromatic | | * | >0.10 | <0.01 |
| Uncharged polar | | | * | <0.001 |
| Charged polar | | | | * |

[1]Statistically significant differences are bolded.

Non-linear Fit to %Buried = (100% - $a$•length$^b$)

| | $a$ | | $b$ | | RMS Deviation |
|---|---|---|---|---|---|
| | Value (%/aa) | Std Error | Value | Std Error | |
| Aliphatic | 192.7 | 23.6 | -0.325 | 0.023 | 4.16 |
| Aromatic | 86.2 | 39.4 | -0.250 | 0.086 | 10.47 |
| Uncharged polar | 83.3 | 9.9 | -0.200 | 0.022 | 3.44 |
| Charged polar | 195.4 | 25.1 | -0.246 | 0.024 | 6.80 |

Data calculated from non-linear fit.

| | At 100 residues | | At 700 residues | |
|---|---|---|---|---|
| | Buried (%) | Slope (100 x %/aa) | Buried (%) | Slope (100 x %/aa) |
| Aliphatic | 56.9 | 14.02 | 77.1 | 1.06 |
| Aromatic | 72.7 | 6.82 | 83.2 | 0.60 |
| Uncharged polar | 56.8 | 6.63 | 77.5 | 0.64 |
| Charged polar | 37.2 | 15.48 | 61.1 | 1.37 |

FIG. 4

| Table 2: Areas & 5 Å Interactions of Side Chain Carboxylate and Amide Groups of Staphylococcal Nuclease ||||||||
|---|---|---|---|---|---|---|---|
| Amino Acid | Seq. No. | In Active Site | Extended (Å²) | Native (Å²) | %Buried | Interactions | Distance (Å) | Type |
| ASP | 19 | Yes | 68.1 | 1.0 | 98.5 | OD2 to Asp21 OD1 | 4.3 | Ionic- |
| | | | | | | OD1 to Gly20 N main | 3.0 | Hbond |
| | | | | | | OE1 to Glu43 OD2 | 4.3 | Ionic- |
| ASP | 21 | Yes | 65.6 | 7.1 | 89.2 | OD1 to Thr22 N main | 3.2 | Hbond |
| | | | | | | OD2 to Glu43 OE1 | 4.5 | Ionic- |
| ASP | 40 | Yes | 69.8 | 40.6 | 41.8 | OD1 to Arg35 NH2 | 3.1 | Ionic+ |
| ASP | 77 | No | 67.2 | 0.0 | 100.0 | OD2 to Tyr91 OH | 2.6 | Hbond |
| | | | | | | OD2 to Thr120 N main | 2.9 | Hbond |
| | | | | | | OD1 to Thr 120 OG1 | 2.6 | Hbond |
| | | | | | | OD2 to Asn118 N main | 4.7 | Hbond |
| ASP | 83 | Yes | 67.2 | 1.5 | 97.8 | OD2 to Arg87 NH2 | 3.1 | Ionic+ |
| | | | | | | OD1 to Arg 87 N main | 2.9 | Hbond |
| | | | | | | OD1 to Arg87 NE | 3.8 | Hbond |
| ASP | 95 | No | 59.5 | 16.1 | 72.9 | OD1 to Lys71 N main | 2.9 | Hbond |
| | | | | | | OD2 to Lys70 N main | 3.1 | Hbond |
| | | | | | | OD1 to Lys70 N main | 3.0 | Hbond |
| GLU | 10 | No | 84.1 | 7.6 | 91.0 | OE1 to Tyr27 OH | 2.7 | Hbond |
| | | | | | | OE1 to Lys28 NZ | 4.1 | Ionic+ |
| | | | | | | OE2 to His8 NE2 | 4.1 | Hbond |
| GLU | 43 | Yes | 98.9 | 41.0 | 58.5 | OE1 to Asp21 OD2 | 4.3 | Ionic- |
| | | | | | | OD2 to Asp19 OE1 | 4.5 | Ionic- |
| | | | | | | OE2 to His46 NE2 | 4.7 | Hbond |
| | | | | | | OE1 to Glu52 OE2 | 4.5 | Ionic- |
| GLU | 52 | No | 93.3 | 19.0 | 79.6 | OE1 to Glu43 N main | 2.6 | Hbond |
| | | | | | | OE1 to Glu52 OE2 | 4.5 | Ionic- |
| | | | | | | OE2 to His46 NE2 | 4.7 | Hbond |
| | | | | | | OE2 to Lys48 NZ | 3.3 | Ionic+ |
| GLU | 57 | No | 93.3 | 46.7 | 49.9 | None | | |
| GLU | 67 | No | 85.6 | 40.1 | 53.2 | OE1 to Lys63 NZ | 3.1 | Ionic+ |
| GLU | 73 | No | 85.3 | 43.7 | 48.8 | None | | |
| GLU | 75 | No | 92.3 | 4.4 | 95.2 | OE1 to Tyr93 OH | 2.6 | Hbond |
| | | | | | | OE1 to His121 NE2 | 3.1 | Hbond |
| | | | | | | OE2 to Lys9 NZ | 3.4 | Ionic+ |
| GLU | 101 | No | 92.3 | 34.1 | 63.1 | OE2 to His124 | 4.8 | Hbond |
| GLU | 122 | No | 92.9 | 29.9 | 67.8 | OE2 to Arg126 NH2 | 3.1 | Ionic+ |
| GLU | 129 | No | 85.2 | 11.8 | 86.2 | OE2 to Val111 N main | 2.8 | Hbond |
| | | | | | | OE2 to Lys133 NZ | 2.8 | Ionic+ |
| GLU | 135 | No | 85.7 | 30.1 | 64.9 | OE1 to Arg105 NH1 | 3.0 | Ionic+ |
| ASN | 68 | No | 107.9 | 81.5 | 24.5 | None | | |
| ASN | 100 | No | 103.7 | 0.0 | 100.0 | OD1 to Ile92 N main | 3.0 | Hbond |
| | | | | | | ND2 to Ala90 O main | 3.5 | Hbond |
| | | | | | | ND2 to Leu37 O main | 2.8 | Hbond |
| ASN | 118 | Near | 102.2 | 7.8 | 92.4 | ND2 to Gln80 O main | 3.0 | Hbond |
| ASN | 119 | No | 102.9 | 29.5 | 71.3 | ND2 to Pro117 O main | 3.2 | Hbond |
| ASN | 138 | No | 99.1 | 44.3 | 55.3 | ND2 to Gln106 O main | 2.6 | Hbond |
| GLN | 30 | No | 114.9 | 83.3 | 27.5 | NE2 to Pro31 O main | 4.2 | Hbond |
| GLN | 80 | Yes | 110.7 | 86.3 | 22.0 | OE1 to Gln80 N main | 2.9 | Hbond |
| GLN | 106 | No | 121.4 | 73.4 | 39.5 | None | | |
| GLN | 123 | No | 113.7 | 55.1 | 51.5 | NE2 to Gln123 O main | 4.1 | Hbond |
| | | | | | | OE1 to Gln123 N main | 4.2 | Hbond |
| GLN | 131 | No | 125.8 | 46 | 63.4 | OE1 to Lys134 NZ | 3.9 | Hbond |

FIG. 5

STABILIZING AND DESTABILIZING PROTEINS

RELATED APPLICATION INFORMATION

This application is a continuation of application Ser. No. 08/971,004, filed Nov. 14, 1997 now abandoned, which claim benefit of Ser. No. 60/030,926 filed Nov. 15, 1996.

FIELD OF THE INVENTION

The present invention relates generally to the fields of protein chemistry, protein structural analysis and protein engineering.

BACKGROUND OF THE INVENTION

In a general way, the forces governing the conformational stability of globular proteins have, for the most part, been identified (Kauzmann, 1959; Dill, 1990; Honig and Yang, 1995. However, their relative and often their absolute roles remain elusive. The interactions that stabilize the folded, native structure sum to a free energy in the range of hundreds of kcal/mole (Kauzmann, 1959; Dill, 1990). Because the sum of the destabilizing forces is within the same range, the net stabilizing free energy is rather small, −5 to −20 kcal/mole (Makhatadze and Privalov, 1995).

SUMMARY OF THE INVENTION

Proteins are molecules that primarily consist of a polypeptide chain. Proteins can be modified in various ways known to those in the art, e.g., proteins can have carbohydrate sidechains or be derivatized to include modified amino acids.

As a group, proteins have a wide variety of functions and activities and can have more than one function or activity. Examples of protein functions and activities include acting as a ligand, a binding receptor, a co-factor, a regulator of gene expression, a fluorophore, a chromophore, an ion pump, a transducer of energy from one form to another, a light energy harvester, and as catalyst in many types of transformations of another molecule, called a substrate, or even themselves. We make no effort to distinguish between a function or an activity, and thus use the terms interchangeably or together.

The subset of proteins that are catalytic proteins are referred to in the art, and herein, as enzymes. These are often the most commercially important proteins and function in processes that produce a product from a substrate in part or wholly through the action of one or more enzymes.

As used herein, the term protein is used to refer to all manner of polypeptide based molecules independent of their additional features or their natural or commercial functions. The term enzyme is reserved for that set of proteins that are catalytically active in the transformation of a substrate molecule or themselves.

When specifically referring to the proteins used in and produced by the methods of this invention particular terms are used in this specification. The terms known protein or native protein are used to describe a protein having an amino acid sequence that will be altered in a method of this invention. A known protein is a protein known to one conducting a method of this invention. A known protein can be a wild-type protein, which is a protein the amino acid sequence of which has not been altered from that found in nature. The term known enzyme is used analogously to the use of known protein. These terms are not used herein to mean that the protein used as the starting material must have an amino acid sequence which was never changed from one that is found in nature, although that will frequently be the case. The amino acid sequence of the starting protein can have been previously altered in a variety of ways. The starting protein will often be a protein the sequence of which was previously altered in a method of this invention. Previously altered proteins are considered known proteins for purposes of this specification.

The term mutant protein is used herein to refer to a protein produced through the application of a method of this invention to a known protein. However, in some context mutant protein is also used to describe a protein reported in the literature. In such cases the use will be understood in context.

We use the term stability to refer to the ability of a protein to resist the effects of various conditions that can cause the protein to denature, i.e. to unfold partly or fully, or to become functionally impaired, non-functional, partially active or inactive. Many conditions can cause proteins to denature or can negatively impact the function or activity of a protein including heat (temperatures above the temperature optimum of the known protein), cold (temperature below the temperature optimum of the known protein), organic and inorganic solvents, co-solvents, co-solutes and pH. Solvents include non-water based liquids, e.g., ethanol. Co-solvents include mixtures of various proportions of solvents and water, e.g, a mixture of ethanol and water. Co-solutes are other molecules in solution along with the protein. Co-solutes can include ions, e.g., $Na^+$, organic and inorganic compounds and their salts, e.g. detergents, urea and Guanidine hydrochloride.

In the simplest case, a mutant protein created by a method according to this invention is considered more stable when compared to the known protein if the mutant protein functions or has activity under conditions where the known protein does not function or is inactive. However, many improvements seen in a mutant protein will be in degree rather than in kind. Therefore, it is also said that a mutant protein created by the application of methods of this invention is more stable when compared to the known protein if the mutant protein can function to a greater extent or have greater activity in the presence of a greater degree of a given condition than the known protein. For example, if the mutant protein functions or has greater activity than the known protein (1) at a given temperature, (2) in the presence of co-solvents or co-solutes or (3) under other conditions that negatively impact the function or activity of the known protein, then the mutant protein is said to be more stable when compared to the known protein.

The term flexibility is used to refer to the freedom of a protein to assume differing conformations. Often, the conformations that a protein can assume are not very different, but this is not always the case as large changes can occur on binding to other molecules.

As used herein, the terms "solvent accessible surface area" or "accessible surface area" are used when referring to atoms exposed on the surface of a protein in native or extended conformation. Solvent accessible surface area and accessible surface area are the locus of points mapped out in two dimensions when a probe, usually 1.4 angstroms in radius, is rolled, computationally, across the van der Waals surface of the molecule. It is thus larger than the van der Waals chemical radius of the molecule, and many parts of the van der Waals surface can not be contacted by a probe of finite size, as described in Lee and Richards (1971). These terms may be abbreviated to "surface area" or even "area"

but these terms are also used to refer to the surface area of atoms generally, i.e., the area of a buried atom is zero. In such cases one will understand the meaning from the context.

It is well established that amino acids are buried to various extents in various places in protein structures.

It is well established that amino acids are buried to various extents in various places in protein structures. This variety can be taken advantage of to tailor the effect of altering, by more or less, the amount of buried charged surface in a protein to achieve a desired result. For ease in discussing the range of burial of amino acids, particular terms are used herein to describe the degree of burial of amino acid residues in the native, or folded, conformation of a protein. Fully buried amino acids are those that are approximately 90% or more buried in the native conformation. Partially buried amino acids are those that are not fully exposed or fully buried. For ease of conceptualization, we often use partially buried to refer to amino acids that are between approximately 10% to approximately 90% buried in the native conformation. Amino acids that are substantially inaccessible to solvents are amino acids that are at least about 50% buried in the native conformation of a known protein as seen in the analysis taught herein.

In this specification we refer to amino acids that are outside of and not interacting with an active site or binding site of a protein. In using this terminology we mean amino acids that directly interact with a substrate in an active site and amino acids that interact to such amino acids in such a way that changing them would negatively impact the activity of the protein. Similarly, we mean amino acids that do not directly interact with a moiety bound in the binding site of a protein and amino acids that interact with such amino acids in such a way that changing them would negatively impact the binding of the moiety. A binding moiety can be another protein, another molecule of the same protein or a non-protein molecule.

By nucleic acid is meant any nucleic acid that can be used by proteins and/or enzymes to synthesize a protein either directly or after transcription. Non-natural nucleotides and internucleotide linkages can be used as desired.

A cell culture is any combination of cells, a medium appropriate for the cells and a suitable growth chamber or vessel. The cells can be bacterial, fungal, yeast, plant or mammalian.

An aspect of this invention is a method of analyzing a known protein and thereafter producing a mutant protein that has reduced flexibility. The reduced flexibility translates to an altered activity or functional profile for the mutant protein as compared to the known protein. Initially, one analyzes the known protein to identify fully or partially buried amino acids having a formal charge which are outside of and do not interact with either an active site or a binding site of the known protein. This is performed by comparing the solvent accessible surface area for each atom of the protein in the native conformation and a modeled fully extended conformation. The comparison enables one to determine if any given amino acid is substantially inaccessible to solvents in the native conformation. Thereafter, one synthesizes a mutant protein in which the amino acid having a formal charge is replaced with an amino acid having no formal charge.

In an embodiment, the mutant protein is synthesized by obtaining a nucleic acid having a sequence that encodes the known protein and altering the sequence to encode for the mutant protein by changing the codon for the amino acid having a formal charge to an amino acid having no formal charge. In a preferred embodiment, the protein is produced in a cell culture.

In another embodiment the protein is an enzyme. In a preferred embodiment the mutant enzyme can have a greater activity than the known enzyme at a temperature above the temperature optimum of the known enzyme.

In another embodiment the mutant protein is more stable than the known protein under one of a variety of conditions that negatively impact the activity or function of the known protein. These conditions can include the presence of co-solutes, co-solvents, heat or pH.

In another embodiment, the mutant protein can have greater resistance to the effect of denaturants such as cold, heat, solvents, co-solvents, co-solutes and pH as compared to the known protein.

In another embodiment, the amino acid having a formal charge is replaced by an isosteric amino acid.

In other embodiments, the amino acid is substantially inaccessible to solvents or fully buried.

Another aspect of this invention is a method of analyzing a known protein and thereafter producing a mutant protein that has increased flexibility. The increased flexibility translates to an altered activity or functional profile for the mutant protein as compared to the known protein. Initially, one analyzes the known protein to identify fully or partially buried amino acids having no formal charge which are outside of and do not interact with either an active site or a binding site of the known protein. This is performed by comparing the solvent accessible surface area for each atom of the protein in the native conformation and a modelled fully extended conformation. The comparison enables one to determine if any given amino acid is substantially inaccessible to solvents in the native conformation. Thereafter, one synthesizes a mutant protein in which the amino acid having no formal charge is replaced with an amino acid having a formal charge.

In an embodiment of this aspect, the mutant protein is synthesized by obtaining a nucleic acid having a sequence that encodes the known protein and altering the sequence to encode for the mutant protein by changing the codon for the amino acid having no formal charge to an amino acid having a formal charge. In a preferred embodiment, the protein is produced in a cell culture.

In another embodiment the protein is an enzyme. In a preferred embodiment the mutant enzyme can have a greater activity than the known enzyme at a temperature below the temperature optimum of the known enzyme.

In another embodiment, the amino acid having no formal charge is replaced by an isosteric amino acid.

In other embodiments, the amino acid is substantially inaccessible to solvents or fully buried.

Further features, embodiments and advantages of the invention will become more fully apparent from a consideration of the following description of the invention when taken together with the drawings.

BRIEF DESCRIPTION OF THE DRAWINGS

FIGS. 2A–2D are graphs depicting the solvent accessible surface areas of charged atomic groups in staphylococcal nuclease. Key: Bars=native structure; filled circles= extended polypeptide; asterisks (*) denote residues which are in or near the active site or which interact with active site residues. Histidine is not included in this figure.

Figure 1A:
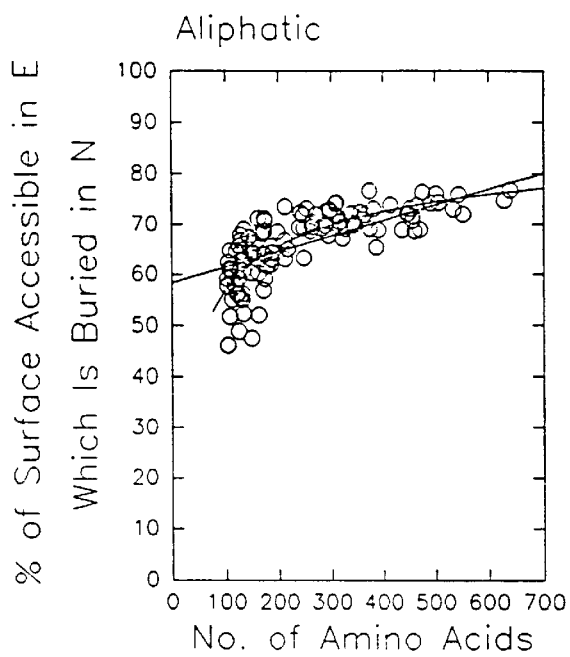
FIGS. 1A–1D are graphs depicting the % of solvent accessible surface area of 124 known protein structures in the extended polypeptide which is buried in the folded polypeptide.
Figure 1B:
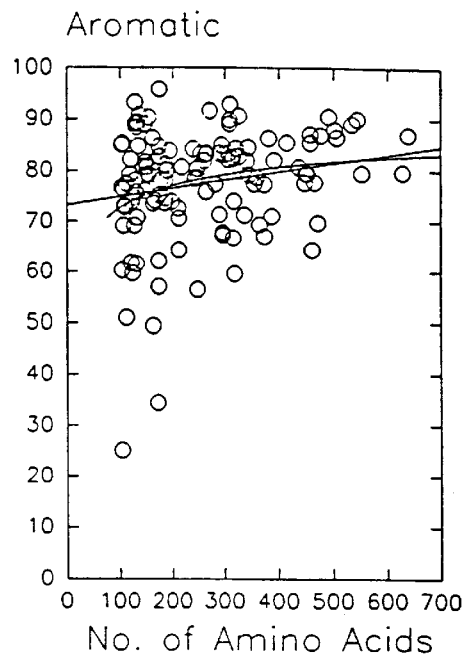
Figure 1C:
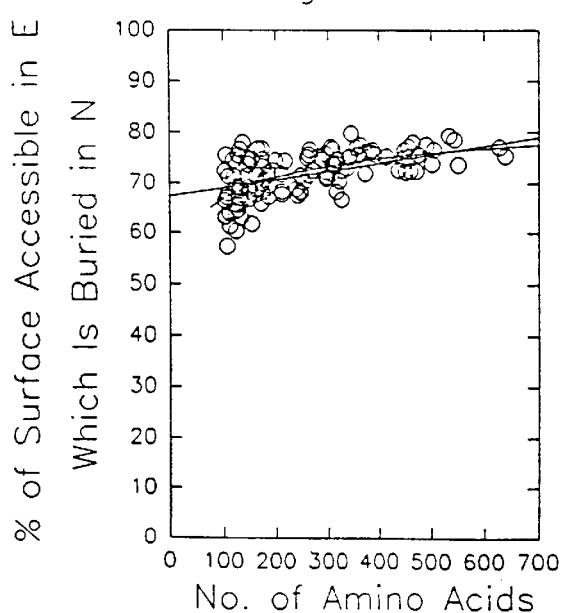

FIGS. 3A–3D are graphs depicting the solvent accessible surface areas of charged atomic groups in muconate lactonizing enzyme. Key: Bars=native structure; filled circles= extended polypeptide; asterisks (*) denote residues which are in or near the active site or which interact with active site residues. Histidine is not included in this figure.

FIG. 4 contains Table 1 depicting the best fit calculated results of the data in FIGS. 1A–1D fitted by least squares to linear and nonlinear functions.

FIG. 5 contains Table 2 depicting the areas and 5 angstrom interactions of side chain carboxylates and amide groups of staphlococcal nuclease.

DESCRIPTION OF THE PREFERRED EMBODIMENTS

The method of the invention allows the systematic modification of a protein, including an enzyme, to create a variant protein with altered activity. For example, the method of the invention permits one to create a variant enzyme that retains greater activity at elevated temperature than the native (i.e., naturally-occurring) form of the protein.

The method of the invention can be used to create a variety of industrially useful variant proteins, including but not limited to enzymatic catalysts. The method can be used to create a variant protein that retains activity under conditions that reduce the activity of the native protein. Thus, the variant protein can be designed to have greater activity than the native form of the protein at elevated temperature, at reduced temperature, in the presence of an inhibitory solvent, or in the presence of an inhibitory solute. Under the unfavorable conditions, the variant form will not necessarily have the same activity as the native form or the protein under favorable conditions. However, the variant form can be useful if under the unfavorable conditions it has greater activity than the native form under the same unfavorable conditions.

The variant proteins are useful, e.g., in food processing, including the preparation of pure food ingredients, in pharmaceutical and chemical production, in the oil industry, and in the production of enzymes for household and industrial detergents. The method can be applied anywhere there is need for protein which are active under conditions which are generally adverse to protein stability and/or function. The method also has applications in the development of high temperature and low temperature protein-based biosensors.

The method of the invention can be used to increase the thermotolerance of a selected protein. Thus, the method can be used to create a variant protein having increased thermophilicity (i.e., increased ability to function at temperatures above that at which the native protein functions or an increased ability to function at or above the optimal temperatures for the native protein). The method can also be used to create a variant protein having increased psychrophilicity (i.e., increased ability to function at temperatures below that at which the native protein functions or an increased ability to function at or below the optimal temperatures for the native protein).

The method of the invention can be used to create variant proteins useful in the food industry. For example, certain processes could be improved if they could proceed at a higher or lower temperature without destabilizing the protein(s) used. For example, the method of the invention can be employed to create high temperature enzymes for the hydrolysis of food proteins (e.g., to make foods more digestible or to create flavor precursors or to hydrolyze starches to produce useful oligosaccharides and sugars). The method of the invention can also be used to create protein useful in the production of pure food ingredients, including flavor molecules. Hydrolases are another group of proteins which can be modified as taught herein. Papain, for example, is used to cleave cereal and meat proteins thereby increasing the concentrations of flavor precursors. A high temperature variant of papain would be useful in the processing of some food materials, and a low temperature variant would be useful for the cold processing of materials which cannot withstand cooking temperatures.

Low temperature variants of proteins can be used to destroy unwanted food constituents. For example, some people are lactose intolerant and prefer dairy products that have been treated by enzymatic digestion to remove lactose. Enzymatic digestion of lactose at room temperatures or at somewhat elevated temperatures exposes products to a risk of bacterial or fungal contamination. Digestion below room temperature could reduce this risk, but many enzymes lose activity at low temperatures. Thus, an enzyme with greater cold tolerance would be useful.

Low temperature lipases are also candidates for industrial use. Enzymatic processing in the food industry has been reviewed by James and Simpson (1996). General reviews of 'extremozymes' have been published recently by Adams (1993), Adams et al. (1995) and Adams and Kelly (1995).

Variant enzymes designed using the method of the invention can be used in the production and processing of pharmaceuticals, in the detoxification of noxious chemicals in contaminated environments either in situ or by processing in enzymatic reactors, in the production and processing of perfumes and industrial fragrances, in the production and processing of industrial chemicals, specialty chemical and specialty biochemicals, in paper processing, in the production of improved performance in detergents (e.g., detergents containing lipases and/or proteases), and in environmental remediation.

The methods of this invention can be applied to create or improve proteins used in biosensors. Ligand binding and/or catalytic properties of proteins can be the basis of sensors to monitor and control industrial processes (e.g., enzymatic or chemical reactions which produce useful materials). Biosensors can be used to monitor the production of a desired product. Biosensors can also be used to monitor production of waste materials which can poison the process and whose control is important for production. However, biosensors can only operate in conditions appropriate for the protein of the sensor. The methods of this invention can be applied to create proteins more closely tailored to function at conditions suitable for the process being monitored or controlled.

The methods of the invention are based on knowledge of the three-dimensional structure of the native protein or a homologue thereof.

A key aspect of the method of the invention is the use of solvent accessible surface area calculations. These calculations entail determining, on an atom by atom basis, the accessible surface area of the protein in each of the following four classes: aliphatic, aromatic, uncharged polar, and charged polar. The solvent accessible surface area in each class is summed and the results for the native conformation (N) subtracted from those for a fully extended polypeptide of the same sequence (E). The term native conformation is used to refer to the conformation of the native protein. The term extended conformation is used to refer to the computer simulated conformation of a maximally extended polypeptide generated as described herein.

In determining the accessible surface area, atoms are classified at follows:

Charged Polar

"Charged polar" atoms include: the terminal C and O of all carboxylates, including those of Asp, Glu and the carboxy terminus, the $N_{zeta}$ of Lys, the amino terminal N, all four atoms of the guanidino group of Arg, including $C_{zeta}$, and the $N_{epsilon2}$ of His and the amino-terminal N. Amino acids that have no formal charge are referred to as uncharged polar, aromatic or hydrophobic. Uncharged polar "Uncharged polar" atoms include: C, O, and N of the peptide bond, the hydroxyl oxygen on Ser, Thr, and Tyr, the $N_{delta1}$, of His, the $N_{epsilon1}$ of Trp, and the three (terminal) atoms of the amide groups of Asn and Gln.

Aromatic

"Aromatic" atoms include: the ring carbons of Phe, Tyr, and Trp, $C_{gamma}$, $C_{delta2}$, and $C_{epsilon1}$ of His; aliphatic: everything else, including $C_{alpha}$. Cofactors such as heme are treated similarly.

This division differs from earlier ones in several ways. Unlike Eisenberg and MacLachlan (1986), the carbons of carboxylate groups and of the guanidino of arginine are counted as part of the charged entity, and, in the same way, the carbon of the peptide and side chain amides is designated uncharged polar. These groups all have pi electrons which are delocalized over the group as a whole, including the carbon. That is why these carbons have $sp^2$ hybridization and why the peptide bond is essentially planar with a large barrier to rotation. The additional surface area added to the uncharged and charged polar areas by these atoms is small, but they are not hydrophobic. The present classification reflects this.

Additionally, it is not assumed that if, for instance, only one oxygen of an Asp was completely exposed to solvent and the other completely buried, the total charge would reside on the exposed oxygen alone because such localization of charge must carry a free energy cost. In such a case Eisenberg and MacLachlan would calculate no buried charged surface, whereas herein, a substantial amount is calculated as buried.

The calculation used in the method of the invention assumes that the free energy of dehydrating a charged group is constant irrespective of how many waters have already been removed.

Matthew's theoretical calculations (1985) suggest that exposure to solvent of only a small percent of a charged group's surface yields a substantial stabilization energy. However, the free energy of water removal from charged groups may not be linear for the accessible surface area buried, unlike hydrophobic free energy (Chothia, 1974; Hermann 1972). In the method of the invention it is preferred to make the assumption that the free energy of dehydration is linear.

Particular amino acids present special cases. The distribution of charge over the entire guanidino group of arginine gives Arg residues a lower charge density than Lys. This may explain why there is a tendency for thermophilic enzymes to have Arg instead of Lys (Perutz and Raidt, 1975; Argos, et al., 1979; Hensel, et al. 1987; Wrba et al., 1990). On the average, the substitutions of Arg for Lys would lower the electrostatic free energy, increasing stability.

Histidine is ambiguous with respect to charge. In the vicinity of neutral pH some are charged, and some are not. In examining a broad array of proteins, this was taken into account by assigning one of the nitrogens as charged and the other as uncharged polar. However, it preferable that each histidine be examined to determine whether or not it is charged. One can look at the partners of histidine and their hydrogen bonding potential to assess whether the His is likely to be charged or not. One can look at whether the partners on each side of the His are H-bond donors or H-bond acceptors. If the partners are H-bond acceptors on both sides, e.g., the His is coordinated to Glu on each side, one can assume that the His is charged, and perform the calculations of surface area accordingly. If however, the His is coordinated with Glu on the one side and an H-bond donor such as Arg on the other, then the His is probably neutral. If the His is coordinated by Ser on each side then, it is probably neutral but it can be charged depending on pH.

One hundred and twenty-four known protein structures were analyzed spanning a size range from 100 to over 600 amino acids (resolution better than or equal to 2.2 Å; R factor better than or equal to 20%) were analyzed. Care was taken to exclude proteins having more than 25% sequence identity. A low end cut-off was imposed to avoid proteins lacking well defined hydrophobic cores. The protein structures analyzed were:

List of the 124 Proteins Used In the Calculations
The Protein Data Bank identifier is given. Each protein entry in the Data Bank is identified by a unique four character identifier.

| 1sha | 1lls | 1hsa | 1btl | rnle |
| --- | --- | --- | --- | --- |
| 1ycc | 1mdc | 1lts | 2cyp | 2nac |
| 1cmb | 1pts | 1rec | 1pda | 2sim |
| 1tro | 1slt | 1gky | 2glt | 6xia |
| 1aaj | 1ecd | 8dfr | 1ezm | 1hle |
| 1fkb | 2fgf | 1dsb | 1abe | 2cpp |
| 2cyr | 1mba | 3adk | 2ctb | 2cts |
| 2trx | 2hbg | 3mds | 1sbp | 1npx |
| 5pal | 1ndk | 2abk | 2gbp | 1alk |
| 2mcm | 1osa | 1mfb | 1ede | 1pii |
| 2tgi | 1cob | 9pap | 2cmd | 2hpd |
| 2mhr | 1l1b | 5gst | 1ads | 5rub |
| 1paz | 1lh1 | 1lte | 1tde | 3grs |
| 2pf1 | 1gpr | 2sga | 2ran | 1nsb |
| 1bp2 | 1cpc | 1mrj | 1lld | 3lad |
| 1bsr | 5tnc | 1bcs | 2pia | 6taa |
| 1rnd | 1cyh | 1ypi | 4ape | 1btc |
| 1acf | 5p21 | 2dnj | xren | 1cgt |
| 1tha | 9wga | 1ca2 | 3pga | 3cox |
| 2ccy | 1bgc | 1arb | 1rib | 1crl |
| 3chy | 2fcr | 2tsc | 1lga | 1thg |
| 1hel | eppa | 3tgl | 1ipd | 1aoz |
| 2aza | 1rbp | 1dri | 2bbk | 1lla |
| 1bbh | 2scp | yppa | 1gox | 1gof |
| 1lfc | 4gcr | 1nar | 1fba | |

The heavy atoms having been classified, extended chains for the 124 proteins in FIGS. 1A–1D were generated from the amino acid sequences in the PDB ATOM records with the program HyperChem (HyperCube, Inc.). The sequences used for generating the extended conformations for FIGS. 1A–1D were obtained from the ATOM records in the Brookhaven Protein Data entries listed above. As there can be discrepancies between the sequence in the ATOM records and the sequence in the SEQRES records, and as ATOM records (and the sequences implicit in them) are used for calculating the native conformation for FIGS. 1A–1D, the calculations are more consistent if performed only using the ATOM records. While the above data is preferred, the observations described herein for solvent accessible surface areas can be seen with any equivalently large and diverse group of protein structures analyzed as shown herein.

The beta-strand conformation of silk defined the backbone except for proline, which was set to the conformation of polyproline II helix and side chains were fully extended (Lee and Richards, 1971). An advantage of using the extended polypeptide chain having the sequence of the native molecule instead of model tripeptides of the form Ala-X-Ala is that effects of the adjacent residues on the accessible surface of each residue are taken into account. Formulations such as Ala-X-Ala to represent the environment of amino acid X in the extended form (Lee and Richards, 1971; Spassov, et al., 1995) have the computational convenience of being a look-up table, but they ignore nearest neighbor effects. The differences are sometimes significant, and the added calculations are not onerous. It is recognized that an unfolded molecule in solution may never assume a fully extended conformation and that the difference between E and N as defined here thus represents an upper limit.

Accessibility calculations can be performed by a variety of programs. The method of Lee and Richards (1971) and the ACCESS program (Richards, 1977) are preferred. The ACCESS program was modified by increasing the array size to accept the very long extended polypeptides. ACCESS generates an output file containing, among other items, one line per atom with the identifying information from the corresponding PDB ATOM record along with the accessibility in $Å^2$ of that atom. A FORTRAN program can be used to group the output of ACCESS as desired. For example, a program named BINS was written to read the ACCESS output file and sort the surface accessible areas into the appropriate "bin" according to whether the atom is aliphatic, aromatic, uncharged polar or charged. BINS or any other program that will perform this function can be used.

In this analysis, amino acid that upon summing have a net charge are referred to as amino acids having a formal charge. Amino acids that do not have a net charge upon summing are referred to as having no formal charge.

Figure 1D:
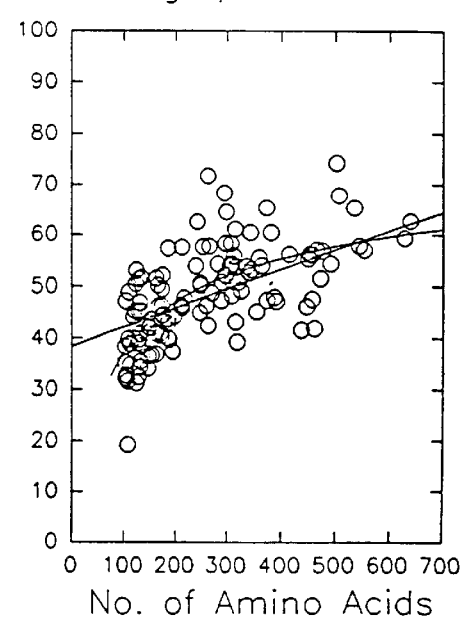

The results are shown in FIGS. 1A–1D. The surface area buried for the four different kinds of atomic surface found in proteins is plotted as a function of protein size for aliphatic atoms (FIG. 1A), aromatic atoms (FIG. 1B), charged polar atoms (FIG. 1C), and uncharged polar atoms (FIG. 1D). Atoms were classified as described above. Cofactors, such as heme, were treated similarly. The percentage surface area buried on folding for a particular protein is calculated as 100(E-N)/E, where E and N are the accessible surface areas of the extended and native forms respectively. Cofactors were included in the calculation of the accessible surface area of the native protein; solvent molecules and substrate molecules were removed. The best-fit straight line and the best-fit curve is shown in FIGS. 1A–1D. Proteins having resolution better than or equal to 2.2 Å and R-factor better than or equal to 20% were chosen from two reduced versions of the protein databank (Bernstein et. al. 1977), the alignment (Overington & Sali, 1994) and FSSP (Holm & Sander, 1994) databases. Initially the alignment database was used to pick one or more non-homologous (less than 25% sequence identity) proteins from each family of proteins. As this database omits families for which only one structure is known, it was augmented with proteins chosen from FSSP.

Typical results for the charged residues of individual proteins are shown in FIGS. 2A–2D and 3A–3D for staphylococcal nuclease and MLE respectively. Histidine is not included in these figures. Each His needs to be examined to see if it might be charged as discussed above. The results support earlier calculations by Rashin and Honig (1984), Chothia (1976), and Janin (1976) on smaller data sets spanning a smaller size range in that Lys and Arg are less likely to be buried than Asp and Glu. Also in agreement with the reports of Rashin and Honig (1984) and Koehl and Delarue (1994), it is now seen that all buried ionic groups are involved in compensating interactions, either hydrogen bonds or interactions with other charges.

An unexpected result is how few of the charged groups have anywhere near as great an exposure in the native form as in the extended. Lee (1991) has presented evidence that the change in solvent accessible surface area upon denaturation is roughly half the difference between the native and fully extended forms. Even when this is taken into account, however, the sequestration of charged surface area shown herein remains considerable, with few residues other than roughly half the lysines having as much exposure in the native as in the unfolded form. It should be noted, moreover, that Lee's result is an average over the whole molecule.

Charged groups are less likely to be as subject to this constraint as other types of group because of the greater free energy cost of dehydrating them. Because of this, charged groups, by their nature, are expected to be more exposed than the Lee average so as to interact with the solvent. Consequently, their accessible surface area in the unfolded state should be closer to that modelled by the fully-extended chain than other residues. Therefore, the error in describing the accessible surface area of charged groups, in the unfolded state by the value calculated for the fully-extended form is less than the area for the other groups on the protein.

From the figures, Lys 6 in the nuclease is an apparent exception. However, this is not the case. Residues 1–5 and 142–149 of the 149 amino acid protein are disordered in the crystal and are not visible in the structure (Hynes and Fox, 1991). Therefore, Lys 6 appears to be the amino terminus and its alpha-amino nitrogen was therefore counted as charged by the computer programs. This is illustrative of how one must be aware that crystallography artifacts, e.g., from embedded disordered sequences, can skew the analysis. One should review the computer output for each position and verify that the interpretation of the data is consistent with other knowledge available about the protein and the environment of the amino acids therein.

Many of the charged groups in FIGS. 2A–2D and 3A–3D are not involved in catalysis or substrate binding. (Those which are so involved are marked with an asterisk.) In staphylococcal nuclease, Asp 77, for example, is completely buried and is not in or near the catalytic center. It makes no salt bridges. It does make three hydrogen bonds: to the side chain OH of Tyr 91 and to the main chain nitrogens of Thr 120 and Asn 118. Its behavior is typical of that described by Rashin and Honig (1984) for buried charges. Several of the glutamic acid carboxylates in staphylococcal nuclease as well as a number of the charged groups in MLE (FIGS. 2B and 3B) behave similarly. MLE Glu 50 is an example of the latter. Like Asp 77 of nuclease, it is buried, it is not in or near the catalytic center, it has no ionic interactions, and it makes three hydrogen bonds, one each to the main chain nitrogens of Gly 305 and Gly 308 and one to the side chain hydroxyl of Thr 52.

The data in FIGS. 1A–1D were fitted by least squares to two functions, linear and nonlinear. The best fit curves are shown in the figure and the calculated results in Table 1. All the linear slopes differ significantly from zero. The dependence of the percentage of surface buried on chain length is steepest for charged groups (0.046%/a.a.). The linear equation does not fit the data very well, which led to the nonlinear fit. The percentage of surface buried [100×(E-N)/E] must tend to 100% as chain length of a globular protein becomes infinite. The surface of E increases linearly with size, while that of N increases as $L^{(2/3)}$ (Chothia, 1976; Janin, 1976, Spassov et al., 1995). The theoretical function is thus $$\% \text{ Buried} = 100 - aL^b \tag{1}$$

where a and b are constants, which were not restrained in the fitting, and L is the chain length. The power function formulation is consistent with other studies of buried surface (Chothia, 1976; Janin, 1976; Spassov et al., 1995).

The nonlinear results show that the difference in slopes for the linear model is due to the more rapid burial of charged and aliphatic surface than aromatic and uncharged polar in the size range from 100 to 200 amino acids. By 700 residues in length all four surface types are buried at the same slow rate. In fact, from 200 amino acids up the slopes are essentially the same (data not shown). Short proteins bury 37% of their charged surface but 57–72% of the other three types. Because burying charged residues or even ion pairs carries an energetic cost, these data indicate that larger proteins are consistently more destabilized by buried charges than smaller ones.

The results are counterintuitive. A general understanding in the art is that in native proteins, charged groups are believed to be on the outside exposed to the aqueous solvent, while hydrophobic groups, by and large, cluster in the interior. This image arose in the early days of protein crystallography, when the only proteins which could be examined were small, viz. myoglobin, lysozyme, and ribonuclease. (Hemoglobin is really four myoglobins from this point of view.) For these proteins it is, indeed, true that most of their charged surface is not buried (Table 1). It is also true that even large proteins have many charged groups exposed to the solvent, or they would not be soluble. The combination maintains the mental image. As the data indicate, however, the simple ideas of charge exposure are inadequate to explain the data in FIGS. 1A–1D. Rashin and Honig (1984) found in their examination of 36 proteins that most bury one or two charges completely. Our results are not inconsistent with theirs but go beyond with the added observations that few charges are fully exposed, and many are heavily sequestered even if not fully buried.

The results reveal a model of how charge burial contributes to maintaining the balance between stabilizing and destabilizing influences for proteins of different sizes. Small proteins with concomitantly small hydrophobic cores and small amounts of hydrophobic stabilization do not need charge burial to be marginally stable. The amount of charged surface buried is therefore low (~40%). Large proteins, with fully formed hydrophobic cores in their domains, bury more charged surface (~65%) to remain appropriately partially stable. The model also shows that proteins smaller than approximately 200 amino acids, while they have hydrophobic cores, the cores are, in a sense, incomplete, reaching full size only for larger molecules and subdividing into domains at still larger chain lengths.

In finding that proteins bury a much larger fraction of their charged surfaces we have demonstrated that the percentage of charged surface area which is solvent accessible in the extended polypeptide but buried in the native form also increases with protein size. Given that there is an unfavorable free energy associated with charge burial, this factor must be added to conformational entropy as a contributor to the balance between stabilizing and destabilizing effects.

Like conformational entropy, the burial of charged surface also has a nonspecific element to it in that it scales more or less smoothly with size. Unlike conformational entropy, however, it has a specific attribute as well in that particular charged groups are buried to particular extents at particular places in the structure. This allows for tailoring of destabilization and thus of conformational flexibility to the particular functional needs of specific proteins.

The amount of buried charge is not correlated with the size or requirements of catalysis or binding sites. Moreover, any charged surface area is buried at a cost in terms of free energy during protein folding. Therefore, a significant fraction of the buried charged surface area is now seen to play an important role in the balance between stability and flexibility in a protein.

From this model of the relationship between stability and flexibility, one would anticipate increased flexibility as a result of the mutation that added a buried charge. This is expected to lead, for instance, to a shift in the temperature of maximum activity to lower values. That is, the substitution can move the enzyme toward becoming a psychrophile.

It should be emphasized that this model does not require the total burial of uncompensated charge. Instead, partial to total sequestration into various types of networks involving ion pairing and/or hydrogen bonding as well as solvent interactions can play a role. This is consistent with Koehl and Delarue's result (1994) that the environment of buried polar surface virtually always contains polar components. The interactions of Asp 77 in staphylococcal nuclease noted herein are an example. Those of all the anionic groups are shown in Table 2.

The methods of this invention are performed in a conceptually straightforward manner. Mutant proteins made by the instant methods are made and examined for effects upon protein function or catalytic activity. We prefer to study thermotolerance, but one can employ any of a broad range of conditions, including variation of temperature, pH, denaturant concentration, and other conditions under which one desires to improve protein performance. For convenience, we often refer only to thermotolerance.

One expects that in most cases stability will be increased by charge removal and decreased by its insertion. One expects also that the concomitant reduction in flexibility upon charge removal will lead to reduced catalytic activity under conditions optimal for the known protein but increased under other conditions.

What distinguishes the present approach and method from that of others is its emphasis on avoidance of the active site or binding site in exploiting the relationship between stability and activity. The key observation is that a larger fraction of charge is buried than previously thought and that this fraction increases with protein size. The fact that there are many more buried charged residues outside of, and not interacting with, the active or binding sites implies that the buried charges are not exclusively related to destabilization of the active site (Shoichet et al., 1995) but have more general effects as well. It is these non-active or -binding site charged residues that can be changed to uncharged residues to increase the overall stability of a protein. From this, the inverse observation arises, namely, that uncharged buried residues that are outside of, and do not interact with, active and binding sites can be changed to charged residues to achieve the opposite effect, i.e., destabilze a protein. With this information it is possible to extend the applicability of the site specific mutagenesis-crystallography-stability-function approach pioneered in the laboratories of, for example, Matthews, Fersht, Craik, and Shortle.

What distinguislhes the present approach and method from that of others is its emphasis on avoidance of the active site or binding site in exploiting the relationship between stability and activity. The key observation is that a larger fraction of charge is buried than previously thought and that this fraction increases with protein size. The fact that there are many more buried charged residues outside of, and not interacting with, the active or binding sites implies that the buried charges are not exclusively related to destabilization of the active site (Shoichet et al., 1995) but have more general effects as well. It is these non-active or -binding site charged residues that can be changed to uncharged residues to increase the overall stability of a protein. From this, the inverse observation arises, namely, that uncharged buried residues that are outside of, and do not interact with active and binding sites can be changed to charged residues to achieve the opposite effect, i.e., destabilize a protein. With this information it is possible to extend the applicability of the site specific mutagenesis-crystallography-stability-function approach pioneered in the laboratories of, for example, Matthews, Fersht, Craik, and Shortle. avoids the ambiguity arising from active site mutations. One cannot know with active site mutations whether the reduced activity is a consequence of reduced flexibility or simply of having disturbed the delicate arrangement of groups essential to binding and catalysis. Therefore, replacement of active or binding site residues is to be avoided. The present conceptual scheme allows us to use the well known free energy cost of charge burial to manipulate stability and flexibility in a more precise way than has been the case.

Because the burial of charged surfaces is destabilizing, the replacement of charged surface by uncharged surface, all other factors being more or less equal, should be stabilizing. The replacement should reduce conformational flexibility, thus reducing catalytic activity. This has broad practical implications for biochemical engineering. Several authors have remarked on the possibility of converting mesophilic enzymes to thermostable forms by site specific mutagenesis (Shoichet, et al., 1995; Mozhaev et al., 1988; Varley and Pain, 1991), which would allow industrial enzymatic processing at elevated temperatures. The instant invention allows one to do exactly that, primarily by replacing carefully chosen charged groups which are not in the active site. By avoiding alterations to the active site one avoids upsetting groups important for binding and catalysis. One therefore expects activity to be reduced owing to reduced flexibility at room temperature but to be restored at elevated temperature (Mozhaev et al., 1988; Varley and Pain, 1991).

The reverse strategy, replacement of uncharged groups by charged ones in carefully chosen areas is used to convert mesophilic enzymes to psychrophiles. Hochachka and Somero (1984) have proposed that psychrophiles are more flexible than their mesophilic counterparts in order to be sufficiently conformationally mobile to catalyze reactions at reasonable rates at psychrophilic temperatures. The method of this invention is used to introduce sequestered charge to make a mutant protein from the known mesophile protein with sufficient flexibility to function or have activity at lower temperatures.

In its purest form, the method of the invention requires knowledge of the three dimensional (3D) structure of the native protein. Although many 3D structures are known, many are not. It is preferable to obtain the 3D structure of the known protein if possible, and there are several routine procedures currently in practice to obtain this information. However, one skilled in the art will recognize that not every structure is presently obtainable, but may become available in the future as technologies progress.

If the 3D structure is not known, there are at least two ways to perform the methods of this invention without direct knowledge of the 3D structure of a protein.

In the first, one takes advantage of the observation that most proteins fall into families of similar structures. Even if the 3D structure of the protein one desires to modify is not known, it is often the case that the structure of a protein from the same family, and thus similar to it, is known. In this case the unknown protein can be modeled on the known one using techniques known to those of skill in the art. This will provide a means of applying the methods to many proteins of unconfirmed structure, but there will remain cases in which no sufficiently homologous structure is known.

A second approach that can be explored when the 3D structure of a known protein of interest is not known relies on the teaching herein that certain types of amino acids are candidates for replacement while others are not. One could replace each such amino acid with an appropriate amino acid to add or delete a charge as desired. However, in this work-around, much more work, however routine, would be required to conduct the method. For example, one would replace many occurrences of amino acids that would not be replaced if the 3D structure were known, as those particular locations would be seen to be in the active site or a binding site or completely exposed. The ultimate result would be a protein of the desired characteristics, but the process of producing it would be less efficient.

These and other means of performing the methods without knowledge of the 3D structure of a protein are possible. However, it will often be preferable to determine the 3D structure of a protein before conducting the methods taught herein to modify the protein. Many methods of determining the 3D structure of a protein are known to those in the art including x-ray crystallography and solution phase nuclear magnetic resonance.

There will be cases in which there are not enough buried residues of the necessary types which are not in the active site such that their replacement will change the protein's thermal stability to the desired level. (This is not a problem in producing a protein to function at low temperature because one will be adding charged residues.) Under such circumstances, partially buried (10–90% exposed) charged residues would be chosen instead. The same criteria as described above would be used to design replacements. Hendsch and Tider (1994) indicate that all ion pairs, no matter how exposed, may be destabilizing in comparison with mutation to hydrophobes. Our analysis extends this to all charged groups, no matter how exposed.

Additionally, one can combine the methods of this invention with other techniques to design a mutant protein by changing other amino acids as well as the few charged ones available. In considering replacement of non-charged amino acids one can be guided as follows. One can look for replacements that provide for better packing of sidechains, replacements that increase the number of hydrogen bonds and or replacements that allow the formation of a disulfide bond which did not previously exist.

However, even with these considerations, a case can arise where this method can not provide a mutant protein with a sufficient reduction in flexibility compared to a known protein for the application desired. One skilled in the art will be able to recognize such a case when presented because in such a case the options for eliminating buried charge will be limited and therefore will limit the applicability of this method.

When performing the methods of this invention, one can also examine the correlation between the solvent accessible surface area of an amino acid residue and the dehydration free energy, i.e.: is it linear or not? If it is not, what is the dependence? The detailed nature of each site is expected, of course, to influence the free energies, so one can examine many sites to average out whatever "noise" there may be. While this analysis is not required to conduct the methods of the invention, the analysis can assist in producing or understanding the stabilizing or destabilizing effects of any given change.

Mutations can be modeled to ensure that they are unlikely to disrupt the protein. Isosteric replacements, that is replacements with residues that closely match the space-filling character of the replaced residues, are preferred because they are expected to be less disruptive. It is also desirable to arrange that as many hydrogen bonding groups, salt bridges, etc. in the environment of the replacement are satisfied as possible (c.f. Koehl and Delarue, 1994). One can replace additional amino acids that interact in the environment of the replacement to achieve that end and-this may commonly be the case. Replacement by hydrophobic residues may also be possible in some cases as with the arc repressor (Waldburger et al., 1995).

All mutants are examined for activity and, by spectroscopic measurements, for native-like folded conformation. Biophysical characterization and enzyme kinetics are done as functions of temperature, pH, denaturant concentration (c.f. Shortle, 1995), and other solution conditions. These measurements can catalog, among other results, the effects of the mutations on thermodynamic stability. Wherever possible, folding kinetics are followed, as well. More than one conformational stressor, e.g. pH and denaturant or pH and temperature, can be varied systematically, other variables being held constant. The resulting maps provide insight into the bases of stability and the effects of the mutations. One should be alert for the occurrence of "molten globule" type states in all experiments. Crystallographic structures of the mutants are determined if the outcome of preliminary biochemical and biophysical characterization indicate that an appropriate result is achieved.

EXAMPLE

The method is described for two proteins: staphylococcal nuclease and muconate lactonizing enzyme (MLE). The nuclease is chosen as a small single domain protein which lacks disulfides. It contains a single tryptophan residue at position 140, which makes it ideal for fluorescence studies. Importantly, there is a rich literature on its thermodynamics and kinetics, including much site specific mutagenesis work (see Shortle, 1995), which is useful in interpreting the data. In having only 149 residues, it is near the low end of the curve of percentage of charged surface buried versus chain length where the slope is steepest (FIGS. 1A–1D).

It was surprising to find that for MLE, 65% of the charged surface which was accessible in E was buried in N (Helin et al., 1995). MLE contains a manganese ion deep within its active site. The cation is coordinated, in part, by side chain carboxylates, which are stabilized, in turn, by cationic side chains. Further analysis, however, showed not only that burying a large charged surface is a general property of proteins, but also that the fraction of charged surface accessible in E and sequestered from solvent in N rises with protein size as described above (FIGS. 1A–1D).

MLE, at 373 residues, buries 65% of its charged surface and is in the region of reduced slope in FIGS. 1A–1D. The kinetics of the MLE catalyzed reaction have been well studied (Avigad et al., 1974; Chari et al., 1987; Gerlt and Gassman, 1992). Although, MLE forms an octamer of identical subunits, both in solution and in the crystal, Helin et al. (1995) have estimated that the interfaces contribute only 10% of the salvation free energy of folding and assembly. Thermodynamic stability measurements therefore will reflect monomer folding primarily. This experiment is performed beginning with native MLE. However, it may be possible to construct a catalytically active monomer, as has been done with triose phosphate isomerase (TIM) (Borchert et al., 1994), the archetype of the alpha/beta barrel class to which MLE belongs. In that case, the monomer can be used.

In one experiment all the Asp, Glu, and Arg residues, having a formal charge, which are not involved in the catalytic mechanism or substrate binding, as well as several lysines are replaced. An effort is made to maintain as many of the polar features of the protein as possible while eliminating the charges. The replacements are hydrophobic or polar amino acids with no formal charge.

One begins by making single site alterations although multiple site mutations can be made. One should observe how far this approach can be pushed in the direction of increased stability and activity by empirical testing. Jaenicke (1991) has pointed out that the additional free energy of stabilization of thermophilic enzymes over the corresponding mesophiles is small (~10 kcal/mol), comparable to the overall stabilization energy of the mesophiles themselves. Although he observes that the differences between the two classes arise from small changes at many points in the molecule, one can invert the observations. The small energy difference between thermostable and ordinary enzymes means that a few altered interactions can be sufficient to provide the extra stabilization (c.f. Adams and Kelly, 1995). Therefore, one should study the effect of each change for added stability, e.g., reduced flexibility, and a neutral to positive effect on activity at e.g., elevated temperatures. These measurements are compared to the native protein.

By examining all non-active site Asp, Glu, and Arg residues having a formal charge in staphylococcal nuclease, for example, one spans a range of solvent accessible surface area per residue from only 29% buried (Arg 81) to 100% buried (Asp 77). Among the glutamates the range is from 49% (Glu 57 & 73) to 91% (Glu 10) (FIGS. 2A–2D and Table 2). MLE has an analogous set of residues to replace.

In a second, reversed experiment, amino acids having no formal charge, of varying surface accessibility are changed to amino acid residues having a formal charge, to destabilize the protein. In the experiment, one studies the effect of each change for decreased stability, e.g., positive effect or activity at, e.g., lower temperatures.

Methods

Both the MLE and staphylococcal nuclease genes have been cloned into overexpression systems. In the case of the nuclease, its gene has been fused to the leader sequence of the *E. coli* outer membrane protein (OmpA), so the bacteria secrete the cloned protein into the medium. The secretory apparatus cleaves the leader, yielding mature nuclease as 40% of the cell's secreted protein (Takahara et al., 1985). This construct was used recently to study the kinetics of signal peptidase I (Chatterjee et al., 1995). The MLE gene has been cloned and expressed in *E. coli* and yields 6–7 mg purified protein per 100 g wet weight of cells (Vollmer, 1995)

Mutagenesis

Site specific mutagenesis is by standard methods reported in the literature, e.g., for mutating pyrophosphatase (Baykov et al., 1995; Käpylä et al., 1995; Salminen et al., 1995; Heikinhcimo et al., 1996; Velichko et al., 1995). Initially, if one desires to make a change with the largest possible effect one should change an amino acid that has very little surface accessible area. For example, in MLE and staphylococcal nuclease, one would first replace amino acids Asp 77 in the nuclease and Glu 50 in MLE. As described above, both are buried, and neither is involved in catalysis or substrate binding, nor do they participate in salt links. For inserting charge into the nuclease, the first candidates for producing the largest change will be Asn100→Asp. If one desired smaller effects, one would replace Asn68→Asp, and Gln106→Glu. The first is fully buried, the second is less than 25% buried, and the third is half buried. These replacements lead to charged residues buried to various degrees, as similarly seen in the replacement of buried Val 66 by a Lys which buried its charge (Stites et al., 1991).

Structural Analysis

Several general methods of obtaining coordinate data for the determination of protein structures are presently in use including crystallography and nuclear magnetic resonance. Where possible, we prefer crystallography.

The refined structures presently known for wild-type MLE (Helin et al., 1995) and staphylococcal nuclease (Hynes and Fox, 1991) are used as the basis for comparisons of wild-type and mutant forms. The mutant proteins are crystallized under conditions similar to the wild-type proteins. To the extent that the proteins do not crystallize under identical conditions, one performs systematic scans close to the conditions under which wild-type protein crystallizes. If such approaches do not yield suitable crystals, one can screen for crystallization starting-points using, e.g., "sparse matrix sampling" (Jancarik & Kim, 1991), where crystallization conditions are chosen based on what has historically worked. One can use the original crystal screen and design additional screens using the crystallization database (Gilliland & Bickam, 1990). The database, is publicly available, currently contains crystallization data for 2353 crystal forms from 1557 different proteins, and is constantly updated. The database is available from Hampton Research Hampton Research Corp., 25431 Cabot Road, Suite 204, Laguna Hills, Calif. 92653 U.S.A.

Diffraction data is collected using detector equipment available to those in the art of macromolecular crystallography. Any suitable equipment can be used, e.g., a Molecular Structures Corporation R-AXIS IIC area detector system mounted on a Rigaku RU200 x-ray generator is satisfactory. For radiation-sensitive crystals, a machine can be equipped with a low-temperature apparatus for "flash-freezing" (Gamblin & Rodgers, 1993). This technique is preferred. One can also endeavor to obtain time at a Synchrotron source (e.g. European Molecular Biology Laboratory, c/o DESY, 22603 Hamburg, German; European Synchrotron Radiation Facility, Boite Postale 220, F-38043, Grenobe, CEDEX, France or the National Synchrotron Light Source, Brookhaven National Laboratory, Box 5000, Upton, N.Y. 11973-5000) for data collection because synchrotrons frequently allow collection of higher-resolution data. For that application, flash-freezing the crystal is strongly recommended.

Small protein structures, that is, those of monomers of approximately 20 kDa or less, can be determined by nuclear magnetic resonance techniques known to those of skill in the art. (Evans, 1995; Wuthrich, 1986) At this time nmr is not preferred for large protein structures, that is, those of monomers of approximately 30 kDa and larger.

If the mutant proteins crystallize in the same space group as the wild-type proteins, solving the structures once the data are collected is a matter of calculating a difference Fourier between wild-type and mutant and refining the new structure, as has been done with phage T4 lysozyme, among others (Eriksson et al., 1992). If the mutant proteins crystallize in new space groups, their structures are preferably determined by a combination of methods of macromolecular crystallography: molecular replacement (Rossmann, 1972) and, if necessary, heavy-atom isomorphous replacement (Blow & Crick, 1959). In general applications one can use the DENZO program ((c) Z. Otwinowski, Yale University) for processing raw frame data; do general crystallographic calculations using the XTALVIEW program ((c) D. E. McRee, Scripps) or the CCP4 program; use the XPLOR program, (Brünger et al., 1987; Brüanger, 1992) for molecular replacement and crystallographic refinement; and use the O program (Jones et al., 1991) for model-building. Other programs available to those in the art can be used as necessary.

Enzyme Assay & Kinetics

Enzyme assays of staphylococcal nuclease are performed by the spectrophotometric method of Cuatrecasas et al. (1969) both for purification and to follow changes in kinetic parameters. MLE is also assayed spectrophotometrically, the method being that of Ngai et al. (1983). Kinetic measurements are performed on a spectrophotometer, e.g., an Aviv Model 17DS UV/Vis instrument.

Thermodynamics of Folding/unfolding

Thermal unfolding is followed spectroscopically by absorbance, fluorescence and circular dichroism. The Aviv 17DS UV/Vis instrument was found to be sensitive and stable enough to detect the absorbance changes of unfolding. Fluorescence measurements include time resolved fluorescence to gain information about segmental motions (Lackowitz, 1983). Acrylamide monomer and molecular oxygen can also be employed as probes of dynamics (Eftink and Ghiron, 1975) and to look for changes wrought by the mutations.

Circular dichroism (CD) can be measured using an instrument such as an Aviv Model 60ADS. An instrument capable of temperature scanning is preferred. Both single wavelength CD scans and spectra as a function of temperature in the near- and far-UV can be employed as needed. The spectral scans can aid in understanding the nature of the conformational transitions (Kahn, 1979). One should always be observant for "molten globule" states (Foygel et al., 1995; for reviews, see Kuwajima, 1989; Christensen and Pain, 1991; Ptitsyn, 1992; Haynie and Freire, 1993; Ptitsyn, 1995). Mutant proteins that assume these states under conformational stress will likely be unsuitable for useful applications.

Guanidine hydrochloride induced unfolding of staphylococcal nuclease can be followed by fluorescence of Trp 140, the only Trp in the molecule (Shortle and Meeker, 1986). It can be particularly important to establish the extent to which mutations act through changes in the stability of the unfolded state rather than the native. This can be detected by a study of m-values, which are the dependence of unfolding free energy on denaturant concentration, d(DG)/d [denaturant] (Shortle, 1995). Although these effects are most easily seen in urea or guanidine denaturation experiments, they are present in thermal unfolding, as well, and can be evaluated in both.

In view of the fact that the methods of this invention involve removing or introducing residues with formal charges, changes in the proton titration behavior of the mutant proteins produced are likely, and these, of course, will contribute to stability. Hydrogen ion titration curves can therefore be examined. In addition, the pH and ionic strength dependence of thermal and denaturant unfolding can also be studied. These and similar "two dimensional" experiments make linkage relations available as tools of thermodynamic analysis (Wyman, 1964).

Scanning microcalorimetry (Privalov, 1979, 1982; Privalov and Gill, 1988; Murphy and Freire, 1992; Makhatadze and Privalov, 1995) can be used to obtain thermodynamic properties directly and can allow sensitive comparisons among mutant proteins and between them and wild type. The correlation of heat capacity data with surface areas can prove to be especially useful (Makhatadze and Privalov, 1990; Spolar et al., 1992). Disagreement of the Van't Hoff enthalpy determined from spectroscopically measured melting with the calorimetric value indicates the presence of folding intermediates (Privalov, 1979) which can differ between wild type and mutant proteins and among the mutants themselves.

The volume change of folding/unfolding is a measure of changes in internal packing in some situations and, especially, of hydration related events (Foygel et al, 1995; Ybe and Kahn, 1994). In favorable cases, in which the folding is on the time scale of minutes, volumetric kinetics can be followed, allowing some of the folding processes to be deconvoluted (Ybe and Kahn, 1994).

REFERENCES

Adams, M. W. W. 1993. Enzymes and proteins from organisms that grow near and above 100° C. *Annu.Rev.Microbiol.* 47: 627–658.

Adams, M. W. W., and Kelly, R. M. 1995. Enzymes from microorganisms in extreme environments. *C&E News*, December 18, pp. 32–42.

Adams, M. W. W., Oerlet, F. B., and Kelly, R. M. 1995. Extremozymes: Expanding the limits of biocatalysis. *Biotechnology* 13: 662–668.

Argos, P., Rossman, M. G., Grau, U. M., Zuber, H., Frank, G., and Tratshin, J. D. 1979. Thermal stability and protein structure. *Biochemistry* 18: 5698–5703.

Avigad, G., Englard, S., Olsen, B. R., Wolfenstein-Todel, C., and Wiggins, R. 1974. Molecular properties of cis, cis-mucronate cycloisomerase from *Pseudomonas putida*. *J.Mol.Biol.* 89: 651–662.

Baykov, A. A., Dudarenkov, V. Y., Kasho, V. N., Kapyla, J., Salminen, T., Hytia, T., Cooperman, B., Goldman, A., and Lahti, R. 1995. Dissociation of hexameric *Escherichia coli* inorganic pyrophosphatase into trimers in Ile136→Gln or His140→Gln substitution and its effect on enzyme catalytic properties. *J.Biol.Chem.* 270: 30804–30812.

Bernstein, F. C. et. al. 1977. The Protein Data Bank: A computer-based archival file for macromolecular structure. *J. Mol. Biol.* 112: 535–542.

Blow, D. M., and Crick, F. H. C. 1959. The treatment of errors in the isomorphous replacement method. *Acta Crystallogr.* 12: 794–802.

Borchert, T. V., Abagyan, R., Jaenicke, R., and Wierenga, R. K. 1994. Design, creation, and characterization of a stable, monomeric triose phosphate isomerase. *Proc. Natl. Acad. Sci. USA* 91: 1515–1518.

Brünger, A. T. 1992. X-PLOR Version 3.1. A system for X-Ray Crystallography and NMR. Yale University Press, New Haven.

Brünger, A. T., Kuriyan, J., and Karplus, M. 1987. Crystallographic R factor refinement by molecular dynamics. *Science* 235: 458–460.

Chari, R. V. J., Whitman, C. P., Kozarich, J. W., Ngai, K.-L., and Ornston, L. N. 1987. Absolute stereochemical course of 3-carboxymuconate cycloisomerases from *Pseudomona putida* and *Acinetobacter calcoasedicus*: analysis and implications. *J.Am.Chem.Soc.* 109: 5514–5519.

Chatterjee, S., D. Suciu, R. E. Dalbey, P. C. Kahn, and M. Inouye. 1995. Determination of Km and $k_{cat}$ for signal peptidase I using a full length secretory precursor, pro-OmpA-nuclease. *J. Mol. Biol.* 245: 311–314.

Chothia, C. 1974. Hydrophobic bonding and accessible surface area in proteins. *Nature* 248: 338–339.

Chothia, C. 1976. The nature of accessible and buried surfaces in proteins. *J. Mol. Biol.* 105: 1–14.

Christensen, H., and Pain, R. H. 1991. Molten globule intermediates and protein folding. *Eur. Biophys. J.* 19: 221–229.

Cuatrecasas, P., Wilchek, M., and Anfinsen, C. B. 1969. The action of staphylococcal nuclease on synthetic substrates. *Biochemistry* 8: 2277–2284.

Dill, K. A. 1990. Dominant forces in protein folding. *Biochemistry* 29: 7133–7155.

Eisenberg, D., and MacLachlan, A. D. 1986. Solvation energy in protein folding and binding. *Nature* 319: 199–203.

Eftink, M. R., and Ghiron, C. A. 1975. Dynamics of a protein matrix revealed by fluorescence quenching. *Proc. Nat. Acad. Sci. USA* 72: 3290–3294.

Eriksson, A. E., Baase, W. A., Zhang, X.-J., Heinz, D. W., Blaber, M., Baldwin, E. P., and Matthews, B. W. 1992. Response of a protein structure to cavity-creating mutations and its relationship to the hydrophobic effect. *Science* 255: 178–183.

Evans, J. N. S. 1995. Biomolecular NMR Spectroscopy, Oxford Univerity Press, Oxford.

Foygel, K., S. Spector, S. Chatterjee, and P. C. Kahn. 1995. The volume changes of the molten globule transitions of horse heart ferricytochrome c: A thermodynamic cycle. *Protein Science* 4: 1426–1429.

Gamblin, S. J., and Rodgers, D. W. 993. In *Proceedings of the 1993 CCP4 Study Weekend*, Daresbury Laboratory, Warrington, UK, 28–32.

Gerlt, J. A., and Gassman, P. G. 1992. Understanding enzyme-catalyzed proton abstraction from carbon acids: details of stepwise mechanisms for b-elimination reactions. *J.Am.Chem.Soc.* 114: 5928–5934.

Gilliland, G. L., and Bickham, D. M. 1990. The biological macromolecular crystallization database: a tool for developing crystallization strategies. In *Methods, A Companion to Methods in Enzymology* 1: 6–11.

Haynie, D. T., and Freire, E. 1993. Structural energetics of the molten globule state. Proteins: *Struct. Funct. Genet.* 16: 115–140.

Heikinhcimo, P., Pohjanjoki, P., Helminen, A., Tasanen, M., Cooperman, B. S., Goldman, A. & Lahti, R. 1996. A site directed mutagenesis study of *Saccharomyces cerevisiae* inorganic pyrophosphatase. Functional conservation of the active site of soluble inorganic pyrophosphatases. *Eur. J. Biochem.*, 239: 11 138–143.

Helin, S., Kahn, P. C., Lakshmi Guha, L., Mallows, D. J., Steitz, T. A., and Goldman, A. 1995. The refined x-ray structure of mucronate lactonizing enzyme from *Pseudomonas putida* at 1.85 A resolution. *J. Mol. Biol.* 254: 918–941.

Hensel, R., Laumann, S., Lang, J., Heumann, H., and Lottspeich, F. 1987. Characterization of two D-glyceraldehyde-3-phosphate dehydrogenases from the extremely thermophylic archaebacterium Thermoproteus tenax. *Eur. J. Biochem.* 170: 325–333.

Hermann, R. B. 1972. Theory of hydrocarbon bonding. II. The correlation of hydrocarbon solubility in water with solvent cavity surface area. *J. Phys. Chem.* 76: 2754–2759.

Hibler, D. W., Stolowich, N. J., Reynolds, M. A., Gerlt, J. A., Wilde, J. A., and Bolton, P. H. 1987. Site directed mutants of staphylococcal nuclease. Detection and localization by $^1$H NMR spectroscopy of conformational changes accompanying substitutions for glutamic acid 43. *Biochemistry* 26: 6278–6286.

Hochachka, P. W., and Somero, G. N. 1984. *Biochemical Adaptations*. Princeton University Press.

Holm, L. & Sander, C. 1994. The FSSP Database of Structurally Aligned Protein Fold Familes. *Nucleic Acids Res.* 22: 3600–3609.

Honig, B., and Yang, A.-S. 1995. Free energy balance in protein folding. *Adv. Prot. Chem.* 46: 27–58.

Hynes, T. R., and Fox, R. O. 1991. The crystal structure of staphylococcal nuclease refined at 1.7 Å resolution. *Proteins: Struct. Funct. Genet.* 10: 92–105.

Jaenicke, R. 1991. Protein stability and molecular adaptation to extreme conditions. *Eur. J. Biochemistry* 202: 715–728.

James, J., and Simpson, B. K. 1996. Applications of enzymes in food processing. *Crit. Rev. Food Sci. Nutr.* 36: 437–453.

Jancarik, J., and Kim, S.-H. J. 1991. Sparse matrix sampling: a screening method for crystallization of proteins. *Appl. Cryst.* 24: 409–411.

Janin, J. 1976. Surface area of globular proteins. *J. Mol. Biol.* 105: 13–14.

Jones, T. A., Zou, J.-Y., Cowan, S. W., and Kjeldgaard, M. 1991. Improved methods for building protein models in electron density maps and the location of errors in these models. *Acta Crystallogr. A* 47: 110–119.

Kahn, P. C. 1979. The interpretation of near ultraviolet circular dichroism. *Meth. Enzymol.* 61: 339–378.

Käpylä, J., Hytia, T., Lahti, R., Goldman, A., Baykov, A. A., and Cooperman, B. S. 1995. The Effect of D97E Substitution on the Kinetic and Thermodynamic Properties of *Escherichia coli* Inorganic Pyrophosphatase. *Biochemistry* 34: 792–800.

Kauzmann, W. 1959. Some factors in the interpretation of protein denaturation. *Adv. Prot. Chem.* 14: 1–63.

Koehl, P., and Delarue, M. 1994. Polar and nonpolar atomic environments in the protein core: Implications for folding and binding. *Proteins: Struct. Funct. Genet.* 20: 264–278.

Kuwajima, K., 1989. The molten globule state as a clue for understanding the folding and cooperativity of globular protein structure. *Proteins: Struct. Funct. Genet.* 6: 87–103.

Lee, B. 1991. Isoenthalpic and isoentropic temperatures and the thromodynamics of protein denaturation. *Proc. Natl. Acad. Sci. USA* 88: 5154–5158.

Lee, B. K., and Richards, F. M. 1971. The interpretation of protein structures: Estimation of static accessibility. *J. Mol. Biol.* 55: 379–400.

Makhatadze, G. I., and Privalov, P. L. 1995. Energetics of protein structure. *Adv. Prot. Chem.* 47: 307–425.

Makhatadze, G. I., and Privalov, P. L. 1990. Heat capacity of proteins I. Partial molar heat capacity of individual amino acid residues in aqueous solution: Hydration effect. *J. Mol. Biol.* 213: 375–384.

Matthew, J. 1985. Electrostatic effects in proteins. *Annu. Rev. Biophys. Biophys. Chem.* 14: 387–417.

Mozhaev, V. V., Berezin, I. V., and Martinek, K. 1988. Structure stability relationship in proteins: fundamental tasks and strategy for the development of stabilized enzyme catalysts for biotechnology. *CRC Crit. Rev. Biochem.* 23: 235–281.

Murphy, K. P., and Freire, E. 1992. Thermodynamics of structural stability and cooperative folding in proteins. *Adv. Prot. Chem.* 43: 313–361.

Ngai, K.-L., Ornston, L. N., and Kallen, R. G. 1983. Enzymes of the b-ketoadipate pathway in *Pseudomonas putida*: Kinetic and magnetic resonance studies of the cis,cis-mucronate cycloisomerase catalyzed reaction. *Biochemistry* 22: 5223–5230.

Overington, J. P. & Sali, A. 1994. Derivation of rules for comparative protein modeling from a database of protein structure alignments. *Prot. Sci.* 3: 1582–1596.

Perutz, M. F., and Raidt, H. 1975. Stereochemical basis of heat stability in bacterial ferredoxins and in haemoglobin A2. *Nature* 255: 256–259.

Privalov, P. L. 1979. Stability of proteins: Small globular proteins. *Adv. Prot. Chem.* 33: 167–241.

Privalov, P. L. 1982. Stability of proteins: Proteins which do not present a single cooperative system. *Adv. Prot. Chem.* 35: 1–104.

Privalov, P. L., and Gill, S. J. 1988. Stability of protein structure and hydrophobic interaction. *Adv. Prot. Chem.* 39: 191–234.

Ptitsyn, O. B. 1992. The molten globule state. In Creighton, T. E., ed. *Protein folding*. Freeman, New York, pp. 243–300.

Ptitsyn, O. B. 1995. Molten globule and protein folding. *Adv. Prot. Chem.* 47: 83–229.

Rashin, A., and Honig, B. 1984. On the environment of ionizable groups in globular proteins. *J. Mol. Biol.* 173: 515–521.

Richards, F. M. 1977. Areas, volumes, packing and protein structures. *Annu. Rev. Biophys. Bioeng.* 6: 151–176.

Rossmann, M. G. 1972. Ed. *The Molecular Replacement Method*, Gordon & Beach, New York, London and Paris.

Salminen, T., Toplyakov, A., Kankare, J., Cooperman, B. S., Laliti, R. & Goldman, A. "An unusual route to thermostability disclosed by the comparison of Thermus thermophilus and *Eschericchia coli* inogranic pyrophosphatases" *Protein Science*, in press, (1996).

Shoichet, B. K., Baase, W. A., Kuroki, R., and Matthews, B. W. 1995. A relationship between protein stability and protein function. *Proc. Natl. Acad. Sci. USA* 92: 452–456.

Shortle, D. 1995. Staphylococcal nuclease: A showcase of m-value effects. *Adv. Prot. Chem.* 46: 217–247.

Shortle, D., and Meeker, A. K. 1986. Mutant forms of staphylococcal nuclease with altered patterns of guanidine hydrochloride and urea denaturation. *Proteins: Struct. Funct. Genet.* 1: 81–89.

Spassov, V. Z., Karshikoff, A. D., and Ladenstein, R. 1995. The optimization of protein-solvent interactions: thermostability and the role of hydrophobic and electrostatic interactions. *Prot.Sci.* 4: 1516–1527.

Spolar, R. S., Livingstone, J. R., and Record, M. T., Jr., 1992. Use of liquid hydrocarbon and amide transfer data to estimate contributions to thermodynamic functions of protein folding from the removal of nonpolar and polar surface from water. *Biochemistry* 31: 3947–3955.

Stites, W. E., Gittis, A. G., Lattman, E. E., and Shortle, D. 1991. In a staphylococcal nuclease mutant the side chain of a lysine replacing valine 66 is fully buried in the hydrophobic core. *J. Mol. Biol.* 221: 7–14.

Takahara, M., Hibler, D. W., Barr, P. J., Gerlt, J. A., and Inouye, M. 1985. The OmpA signal peptide directed secretion of staphylococcal nuclease A by *Escherichia coli*. *J. Biol. Chem.* 260: 2670–2674.

Varley, P. G., and Pain, R. 1991. Relation between stability, dynamics and enzyme activity in 3-phosphoglycerate kinases from yeast and *Thermus thermophilus*. *J. Mol. Biol.* 220: 531–538.

Velichko, I. V., Volk, S. E., Dudarenkov, V. Yu., Magrelova, N. N., Chernyak, V. Ya., Goldman, A., Cooperman, B. S., Lahti, R., and Daykov, A. A. 1995. Cold lability of mutant forms of *Escherichia coli* inorganic pyrophosphatase. *FEBS Lett.*, 359: 20–22.

Vollmer, M. D. 1995. Die katalytischen Eigenschaften der Muconat- und Chloromuconat-Cycloisomerasen: Analyse der Unterschiede und Implicationen für die Evolution. Ph. D. Thesis, Universität Stuttgart.

Waldburger, C. D., Schildback, J. F., and Sauer, R. T. 1995. Are buried salt bridges important for protein stability and conformational specificity? *Struct. Biol.* 2: 122–128.

Waldburger, C. D., Jonsson, T., and Sauer, R. T. 1996. Barriers to protein folding: Formation of buried polar interactions is a slow step in acquisition of structure. *Proc. Natl Acad. Sci. USA* 93: 2629–2634.

Warshel, A. 1978. Energetics of enzyme catalysis. *Proc. Natl Acad. Sci. USA* 75: 5250–5254.

Warshel, A., Sussman, F., and Hwang, J.-K. 1988. Evaluation of catalytic free energies in genetically modified proteins. *J. Mol. Biol.* 201: 139–159.

Wrba, A., Schweighr, A., Schultes, V., Jaenicke, R., and Závodszky, P. 1990. Extremely thermostable D-glyceraldehyde-3-phosphate dehydrogenase from the eubacterium Thermotoga maritima. *Biochemistry* 29: 7584–7592.

Wuthrich, K. 1986. NMR of Proteins and Nucleic Acids, Wiley, New York.

Wyman, J. 1964. Linked functions and reciprocal effects in hemoglobin: A second look. *Adv. Prot. Chem.* 19: 224–286.

Ybe, J., and P. C. Kahn. 1994. Slow folding kinetics of ribonuclease-A by volume change and circular dichroism: Evidence for two independent reactions. *Protein Science* 3: 638–649.

Zhi, W., Srere, P. A., and Evans, C. T. 1991. Conformational stability of pig citrate synthase and some active site mutants. *Biochemistry* 30: 9281–9286.

---

What is claimed is:

1. A method of designing a variant of a selected wild-type protein that is a candidate for having increased thermophilicity compared to the wild-type protein, comprising:

a) providing the atomic coordinates of the selected wild-type protein in its folded conformation;

b) using the atomic coordinates to calculate a first solvent accessible surface area for each polar charged atom of the selected wild-type protein when the selected wild-type protein is in its folded conformation;

c) calculating a first sum, the first sum being the sum of the first solvent accessible surface areas of the polar charged atoms for an amino acid having a formal charge wherein the amino acid is outside of an active site of the selected wild-type protein and does not interact with an active site of the selected wild-type protein;

d) calculating a second solvent accessible surface area for each polar charged atom in the selected wild-type protein when the protein is in an extended conformation;

e) calculating a second sum, the second sum being the sum of the second solvent accessible surface areas of the polar charged atoms for the amino acid having a formal charge;

f) determining that the amino acid having a formal charge is at least partially buried when the first sum is less than the second sum by at least 29%; and g) designing a variant protein that is a candidate for having increased thermophilicity compared to the wild-type protein by replacing one or more at least partially buried amino acids with an amino acid having no formal charge.

2. The method of claim 1, wherein at least one of the partially buried amino acids is replaced with an isosteric amino acid.

* * * * *

SEQUENCE LISTING

<160> NUMBER OF SEQ ID NOS: 2

<210> SEQ ID NO 1
<211> LENGTH: 373
<212> TYPE: PRT
<213> ORGANISM: Pseudomonas putida

<400> SEQUENCE: 1

```
Met Thr Ser Ala Leu Ile Glu Arg Ile Asp Ala Ile Ile Val Asp Leu
 1               5                  10                  15

Pro Thr Ile Arg Pro His Lys Leu Ala Met His Thr Met Gln Gln Gln
                20                  25                  30

Thr Leu Val Val Leu Arg Val Arg Cys Ser Asp Gly Val Glu Gly Ile
            35                  40                  45

Gly Glu Ala Thr Thr Ile Gly Gly Leu Ala Tyr Gly Tyr Glu Ser Pro
    50                  55                  60

Glu Gly Ile Lys Ala Asn Ile Asp Ala His Leu Ala Pro Ala Leu Ile
65                  70                  75                  80

Gly Leu Ala Ala Asp Asn Ile Asn Ala Ala Met Leu Lys Leu Asp Lys
                85                  90                  95

Leu Ala Lys Gly Asn Thr Phe Ala Lys Ser Gly Ile Glu Ser Ala Leu
            100                 105                 110

Leu Asp Ala Gln Gly Lys Arg Leu Gly Leu Pro Val Ser Glu Leu Leu
        115                 120                 125

Gly Gly Arg Val Arg Asp Ser Leu Glu Val Ala Trp Thr Leu Ala Ser
    130                 135                 140

Gly Asp Thr Ala Arg Asp Ile Ala Glu Ala Arg His Met Leu Glu Ile
145                 150                 155                 160

Arg Arg His Arg Val Phe Lys Leu Lys Ile Gly Ala Asn Pro Val Glu
                165                 170                 175

Gln Asp Leu Lys His Val Val Thr Ile Lys Arg Glu Leu Gly Asp Ser
            180                 185                 190

Ala Ser Val Arg Val Asp Val Asn Gln Tyr Trp Asp Glu Ser Gln Ala
        195                 200                 205

Ile Arg Ala Cys Gln Val Leu Gly Asp Asn Gly Ile Asp Leu Ile Glu
    210                 215                 220

Gln Pro Ile Ser Arg Ile Asn Arg Gly Gly Gln Val Arg Leu Asn Gln
225                 230                 235                 240

Arg Thr Pro Ala Pro Ile Met Ala Asp Glu Ser Ile Glu Ser Val Glu
                245                 250                 255
```

```
Asp Ala Phe Ser Leu Ala Ala Asp Gly Ala Ala Ser Ile Phe Ala Leu
            260                 265                 270
Lys Ile Ala Lys Asn Gly Gly Pro Arg Ala Val Leu Arg Thr Ala Gln
            275                 280             285
Ile Ala Glu Ala Ala Gly Ile Gly Leu Tyr Gly Gly Thr Met Leu Glu
            290                 295             300
Gly Ser Ile Gly Thr Leu Ala Ser Ala His Ala Phe Leu Thr Leu Arg
305                 310                 315                 320
Gln Leu Thr Trp Gly Thr Glu Leu Phe Gly Pro Leu Leu Leu Thr Glu
                325                 330                 335
Glu Ile Val Asn Glu Pro Pro Gln Tyr Arg Asp Phe Gln Leu His Ile
            340                 345                 350
Pro Arg Thr Pro Gly Leu Gly Leu Thr Leu Asp Glu Gln Arg Leu Ala
            355                 360                 365
Arg Phe Ala Arg Arg
        370

<210> SEQ ID NO 2
<211> LENGTH: 149
<212> TYPE: PRT
<213> ORGANISM: Staphylococcus sp.

<400> SEQUENCE: 2

Ala Thr Ser Thr Lys Lys Leu His Lys Glu Pro Ala Thr Leu Ile Lys
1               5                   10                  15
Ala Ile Asp Gly Asp Thr Val Lys Leu Met Tyr Lys Gly Gln Pro Met
            20                  25                  30
Thr Phe Arg Leu Leu Leu Val Asp Thr Pro Glu Thr Lys His Pro Lys
            35                  40                  45
Lys Gly Val Glu Lys Tyr Gly Pro Glu Ala Ser Ala Phe Thr Lys Lys
        50                  55                  60
Met Val Glu Asn Ala Lys Lys Ile Glu Val Glu Phe Asp Lys Gly Gln
65                  70                  75                  80
Arg Thr Asp Lys Tyr Gly Arg Gly Leu Ala Tyr Ile Tyr Ala Asp Gly
                85                  90                  95
Lys Met Val Asn Glu Ala Leu Val Arg Gln Gly Leu Ala Lys Val Ala
            100                 105                 110
Tyr Val Tyr Lys Pro Asn Asn Thr His Glu Gln His Leu Arg Lys Ser
            115                 120                 125
Glu Ala Gln Ala Lys Lys Glu Lys Leu Asn Ile Trp Ser Glu Asp Asn
            130                 135                 140
Ala Asp Ser Gly Gln
145
```